(12) United States Patent
McKenna et al.

(10) Patent No.: US 7,037,936 B2
(45) Date of Patent: May 2, 2006

(54) COMPOUNDS USEFUL FOR THE TREATMENT OF CANCER, COMPOSITIONS THEREOF AND METHODS THEREWITH

(75) Inventors: Jeffrey McKenna, San Diego, CA (US); Frank Mercurio, San Diego, CA (US); Veronique Plantevin, San Diego, CA (US); Weilin Xie, San Diego, CA (US); Michele Pagano, New York, NY (US)

(73) Assignee: Signal Pharmaceuticals, LLC., San Diego, CA (US)

( * ) Notice: Subject to any disclaimer, the term of this patent is extended or adjusted under 35 U.S.C. 154(b) by 0 days.

(21) Appl. No.: 10/463,009

(22) Filed: Jun. 16, 2003

(65) Prior Publication Data

US 2006/0030617 A1    Feb. 9, 2006

Related U.S. Application Data

(60) Provisional application No. 60/389,461, filed on Jun. 17, 2002.

(51) Int. Cl.
  *A61K 31/35* (2006.01)
(52) U.S. Cl. .................................... 514/451
(58) Field of Classification Search .............. 514/451
  See application file for complete search history.

(56) References Cited

U.S. PATENT DOCUMENTS 3,328,249 A * 6/1967 Aceto et al. ............... 514/649

FOREIGN PATENT DOCUMENTS

| WO | WO 93/15047 | 8/1993 |
| WO | WO 00/12679 | 3/2000 |
| WO | WO 00/34447 | 6/2000 |
| WO | WO 02/55665 | 7/2002 |

OTHER PUBLICATIONS

Goldman et al. (Editors) "Principles of Cancer Therapy". Cecil's Textbook of Medicine (Twenty-First Edition). W.B. Saunders Company, 2000. p. 1060-1074.*
STN Accession No. 1982:199191. Leclerc et al. "Synthesis and Cardiovascular Activity of a New Series of Cyclohexylaralkylamine Derivatives Related to Perhexiline". Journal of Medicinal Chemistry. 1982; 25(6); 709-714. (pp. 1-11).*
STN Accession No. 1967:499834. Aceto et al. "Compounds for Counteracting Depressive States". Abstract of U.S. Patent No. 3328249 Issued 1967. (pp. 1-7).*
Alessandrini et al., 1997, "Regulation of the cyclin-dependent kinase inhibitor p27 by degradation and phosphorylation," Leukemia. 11(3):342-345. Review.
Ganoth et al., 2001, "The cell-cycle regulatory protein Cks1 is required for SCF(Skp2)-mediated ubiquitinylation of p27, " Nat Cell Biol. 3(3):321-324.
Goukassian et al., 2001, "Overexpression of p27(Kip1) by doxycycline-regulated adenoviral vectors inhibits endothelial cell proliferation and migration and impairs angiogenesis," FASEB J. 15(11):1877-1885.
Kwon et al., 1997, "Overexpression of cyclin E and cyclin-dependent kinase inhibitor (p27Kip1): effect on cell cycle regulation in HeLa cells," Biochem Biophys Res Commun. 238(2):534-538.
Pagano, 1997, "Cell cycle regulation by the ubiquitin pathway," FASEB J. 11(13):1067-1075, Review.
Pagano et al., 1995, "Role of the ubiquitin-proteasome pathway in regulating abundance of the cyclin-dependent kinase inhibitor p27," Science 269(5224):682-685.
Sheaff et al., 1997, "Cyclin E-CDK2 is a regulator of p27Kip1," Genes Dev. 1997 11(11):1464-1478.
Yu et al., 1998, "Human CUL-1 associates with the SKP1/SKP2 complex and regulates p21 (CIP1/WAF1) and cyclin D proteins," Proc Natl Acad Sci U S A. 95(19):11324-11329.

* cited by examiner

*Primary Examiner*—Christopher S. F. Low
*Assistant Examiner*—Leslie A Royds
(74) *Attorney, Agent, or Firm*—Jones Day

(57) ABSTRACT

The present invention generally relates to compounds and compositions useful for the modulation of ligase activity. The invention further relates to Compounds of the Invention, compositions thereof, and methods for treating or preventing cancer, a neoplastic disorder, acute or chronic renal failure, an inflammatory disorder, an immune disorder, a cardiovascular disease, an effect of aging or an infectious disease comprising administering an effective amount of a Compound of the Invention. The invention further relates to the use of a Compound of the Invention as a preservative of a cell, blood, tissue or an organ or as an agent to modulate stem cells.

2 Claims, No Drawings

COMPOUNDS USEFUL FOR THE TREATMENT OF CANCER, COMPOSITIONS THEREOF AND METHODS THEREWITH

This application claims the priority benefit of U.S. application No. 60/389,461, filed Jun. 17, 2002, which is incorporated by reference herein in its entirety.

1. FIELD OF THE INVENTION

The present invention generally relates to novel compounds and pharmaceuticals compositions useful for the modulation of ligase activity. The invention further relates to methods for treating or preventing cancer, a neoplastic disorder, acute or chronic renal failure, an inflammatory disorder, an immune disorder, a cardiovascular disease, an effect of aging or an infectious disease comprising administering an effective amount of a Compound of the Invention to a patient in need thereof. The invention further relates to the use of a Compound of the Invention as a preservative of a cell, blood, tissue or an organ or as an agent to modulate stem cells.

2. BACKGROUND OF THE INVENTION

Ubiquitin-mediated proteolysis is an important pathway of non-lysosomal protein degradation which controls the destruction of many cellular regulatory proteins including p27, p53, p300, cyclins, E2F, STAT-1, c-Myc, c-Jun, EGF receptor, IkBa, NfkB and b-catenin (Pagano (1997) FASEB J. 11:1067). Ubiquitin is a highly conserved 76-amino acid polypeptide that is present in eukaryotic cells. The ubiquitin pathway leads to the covalent attachment of a polyubiquitin chain to target substrates that are then degraded by a multi-catalytic proteasome complex (Goldberg et al. (1995) Science 269:682–685). Many of the steps regulating protein ubiquitination are known. Initially, the ubiquitin activating enzyme (E1) catalyzes the formation of a high-energy thioester bond with ubiquitin, which is then transferred to a reactive cysteine residue of one of many ubiquitin conjugating enzymes. The final transfer of ubiquitin to an e-amino group or a reactive lysine residue in the target protein occurs in a reaction that need not require an ubiquitin ligase (E3) protein.

p27/Kip1 is a cyclin-dependent kinase (CDK) inhibitor that is predominantly regulated through the ubiquitin-mediated proteolytic pathway. The degradation of the regulatory protein p27/Kip1 appears to be required for $G_1$-to-S phase transition (Sheaffet al. (1997) Genes Dev. 11:1464–1478). In both S-phase kinase-associated protein 2 (SKP2) and cyclin-dependent kinase subunit 1 (CKS1) knockout mice, p27/Kip1 was accumulated to high levels and proliferating cells were arrested in $G_1$ to S-phase transition. Additionally, overexpression of p27/Kip1 in Hela cells resulted in growth inhibition that was associated with cell cycle $G_1$ arrest (Tang and Nordin (1997) Bioch. and Biophys. Res. Comm. 238: 534–538). Overexpression of p27/Kip1 also induced cell cycle arrest in $G_1$ phase and subsequent apoptosis in HCC-9204 cell line (human hepatocellular carcinoma) and lung cancer (Yu et al. (1998) PNAS 95: 11324–11329). Furthermore, overexpression of p27/Kip1 has an anti-angiogenesis effect (Goukassian et al. (2001) FASEB J. 15:1877–1885).

The phosphorylation of p27/Kip1 on $Thr^{187}$ by CDK2 creates a binding site for a SKP2 containing E3 ubiquitin-protein ligase known as skp1-cull-f-box ("SCF") protein. Subsequent ubiquitination of p27/Kip1 by SCF results in the degradation of p27/Kip1 by the proteasome complex (Alessandrini et al. (1997) Leukemia 11:342–345). Additionally, SKP2, which functions as the receptor component of the SCF1 ubiquitin ligase complex, binds to p27/Kip in conjunction with CKS1 only when $Thr^{187}$ of p27/Kip1 is phosphorylated. This critical binding and interaction appears to be necessary for the ubiquitination and degradation of p27/Kip1. Thus, the modulation of the ubiquitination of p27/Kip1 by E3 ubiquitin-protein ligase, which subsequently leads to degradation of p27/Kip1, provides an opportunity for the treatment and prevention of cancer, neoplastic and other proliferative diseases.

In addition, compounds with the general ability to suspend cells at a point in the cell-cycle without adversely affecting the long-term viability of the cell are useful as preservatives of a cell, blood, tissue or an organ in need of such preservation. As much as 60% of stored human blood and blood-products can be lost due to the limited "shelf-life". The degradation in biological products such as whole cells is a result of catabolic processes at the cellular level and is inversely proportional to the storage temperature. A compound that can arrest cells in the G1 phase can increase the "shelf-life" of biological products or allow the biological products to be stored or transferred at elevated temperatures without an increase in the catabolic rate. Thus, there remains a need for compounds with the ability to preserve biological products.

2.1. Cancer and Neoplastic Disease

Cancer affects approximately 20 million adults and children worldwide, and this year, more than 9 million new cases will be diagnosed (International Agency for Research on Cancer). According to the American Cancer Society, about 563,100 Americans are expected to die of cancer this year, more than 1500 people a day. Since 1990, in the United States alone, nearly five million lives have been lost to cancer, and approximately 12 million new cases have been diagnosed.

Currently, cancer therapy involves surgery, chemotherapy and/or radiation treatment to eradicate neoplastic cells in a patient (see, for example, Stockdale, 1998, "Principles of Cancer Patient Management", in Scientific American: Medicine, vol. 3, Rubenstein and Federman, eds., Chapter 12, Section IV). All of these approaches pose significant drawbacks for the patient. Surgery, for example, may be contraindicated due to the health of the patient or may be unacceptable to the patient. Additionally, surgery may not completely remove the neoplastic tissue. Radiation therapy is effective only when the irradiated neoplastic tissue exhibits a higher sensitivity to radiation than normal tissue, and radiation therapy can also often elicit serious side effects. (Id.) With respect to chemotherapy, there are a variety of chemotherapeutic agents available for treatment of neoplastic disease. However, despite the availability of a variety of chemotherapeutic agents, chemotherapy has many drawbacks (see, for example, Stockdale, 1998, "Principles Of Cancer Patient Management" in Scientific American Medicine, vol. 3, Rubenstein and Federman, eds., Ch. 12, sect. 10). Almost all chemotherapeutic agents are toxic, and chemotherapy causes significant, and often dangerous, side effects, including severe nausea, diarrhea, bone marrow depression, immunosuppression, etc. Additionally, many tumor cells are resistant or develop resistance to chemotherapeutic agents through multi-drug resistance.

Therefore, there is a significant need in the art for novel compounds and compositions, and methods that are useful for treating or preventing cancer or neoplastic disease with reduced or without the aforementioned side effects. Further, there is a need for cancer treatments that provide cancer-cell-specific therapies with increased specificity and decreased toxicity.

Citation or identification of any reference in Section 2 of this application is not an admission that such reference is available as prior art to the present invention.

3. SUMMARY OF THE INVENTION

The present invention relates to Compounds of the Invention such as Compounds of Formula (I):

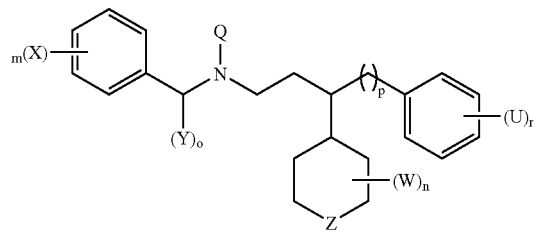

wherein the variables are as defined below, including prodrugs, clathrates, hydrates, solvates, polymorphs and pharmaceutically acceptable salts thereof.

The present invention also relates to pharmaceutical compositions comprising an effective amount of a Compound of the Invention.

The Compounds of the Invention and compositions thereof are useful for modulating ligase activity; treating or preventing a disease responsive to the modulation of ligase activity; treating or preventing a disease responsive to the inhibition of ligase activity; treating or preventing a disease responsive to the activation of ligase activity; modulating E3 ubiquitin-protein ligase activity; modulating E3 ubiquitin-protein ligase mediated ubiquitination of p27/Kip1; modulating cellular p27/Kip1; arresting the growth of a cell; treating or preventing side-effects associated with chemotherapy or radiation therapy; increasing the lifetime of a cell, blood, tissue, an organ or an organism that is cryopreserved; regulating and controlling the differentiation and maturation of mammalian, particularly human stem cells along specific cell and tissue lineages, in particular, to the differentiation of embryonic-like stem cells originating from a postpartum placenta or for the differentiation of stem cells isolated form sources such as cord blood; treating or preventing cancer or neoplastic disease in a patient in need of such treatment or prevention; or inhibiting the growth of a cancer cell or neoplastic cell.

The invention further relates to methods for treating or preventing cancer, a neoplastic disorder, acute or chronic renal failure, an inflammatory disorder, an immune disorder, a cardiovascular disease, an effect of aging or an infectious disease comprising administering an effective amount of a Compound of the Invention to a patient in need thereof. The invention further relates to the use of a Compound of the Invention as a preservative of a cell, blood, tissue or an organ or as an agent to modulate stem cells.

4. DETAILED DESCRIPTION OF THE INVENTION

4.1. Definitions

As used herein, the term "patient" means an animal, preferably a mammal such as a non-primate (e.g., cow, horse, sheep, pig, chicken, turkey, quail, cat, dog, mouse, rat, rabbit or guinea pig) or a primate (e.g., monkey and human), most preferably a human.

"Alkyl" means a saturated straight chain (unbranched) or branched non-cyclic hydrocarbon having from 1 to 10 carbon atoms. "Lower alkyl" means alkyl, as defined above, having from 1 to 4 carbon atoms. Representative saturated straight chain (unbranched) alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like.

"Alkenyl" means a straight chain or branched non-cyclic hydrocarbon having from 2 to 10 carbon atoms and including at least one carbon—carbon double bond. Representative straight chain and branched ($C_2$–$C_{10}$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like. An alkenyl group can be unsubstituted or substituted. A "cyclic alkylidene" is a ring having from 3 to 8 carbon atoms and including at least one carbon—carbon double bond, wherein the ring can have from 1 to 3 heteroatoms.

"Alkynyl" means a straight chain or branched non-cyclic hydrocarbon having from 2 to 10 carbon atoms and including at least one carbon—carbon triple bond. Representative straight chain and branched —($C_2$–$C_{10}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like. An alkynyl group can be unsubstituted or substituted.

The terms "Halogen" and "Halo" mean fluorine, chlorine, bromine or iodine.

"Haloalkyl" means an alkyl group, wherein alkyl is defined above, substituted with one or more halogen atoms, including —$CH_2F$, —$CH_2Cl$, —$CH_2Br$, —$CH_2I$, —$(CH_2)_2F$, —$(CH_2)_2Cl$, —$(CH_2)_2Br$, —$(CH_2)_2I$, —$CF_3$, —$CH_2CF_3$, —$(CH_2)_2CF_3$ and the like.

"Acyloxy" means an —OC(O)alkyl group, wherein alkyl is defined above, including —$OC(O)CH_3$, —$OC(O)CH_2CH_3$, —$OC(O)(CH_2)_2CH_3$, —$OC(O)(CH_2)_3CH_3$, —$OC(O)(CH_2)_4CH_3$, —$OC(O)(CH_2)_5CH_3$, and the like.

"Alkoxy" means —O-(alkyl), wherein alkyl is defined above, including —OCH$_3$, —OCH$_2$CH$_3$, —O(CH$_2$)$_2$CH$_3$, —O(CH$_2$)$_3$CH$_3$, —O(CH$_2$)$_4$CH$_3$, —O(CH$_2$)$_5$CH$_3$, and the like.

"Lower alkoxy" means —O-(lower alkyl), wherein lower alkyl is as described above.

"Aryl" means a carbocyclic aromatic group containing from 5 to 10 ring atoms. Representative examples include, but are not limited to, phenyl, tolyl, anthracenyl, fluorenyl, indenyl, azulenyl, pyridinyl and naphthyl, as well as benzo-fused carbocyclic moieties including 5,6,7,8-tetrahydronaphthyl. A carbocyclic aromatic group can be unsubstituted or substituted. In one embodiment, the carbocyclic aromatic group is a phenyl group.

"Cycloalkyl" means a monocyclic or polycyclic saturated ring having carbon and hydrogen atoms and having no carbon—carbon multiple bonds. Examples of cycloalkyl groups include, but are not limited to, (C$_3$–C$_7$)cycloalkyl groups, including cyclopropyl, cyclobutyl, cyclopentyl, cyclohexyl, and cycloheptyl, and saturated cyclic and bicyclic terpenes. A cycloalkyl group can be unsubstituted or substituted. In one embodiment, the cycloalkyl group is a monocyclic ring or bicyclic ring.

"Mono-alkylamino" means —NH(alkyl), wherein alkyl is defined above, such as —NHCH$_3$, —NHCH$_2$CH$_3$, —NH(CH$_2$)$_2$CH$_3$, —NH(CH$_2$)$_3$CH$_3$, —NH(CH$_2$)$_4$CH$_3$, —NH(CH$_2$)$_5$CH$_3$, and the like.

"Di-alkylamino" means —N(alkyl)(alkyl), wherein each alkyl is independently an alkyl group as defined above, including —N(CH$_3$)$_2$, —N(CH$_2$CH$_3$)$_2$, —N((CH$_2$)$_2$CH$_3$)$_2$, —N(CH$_3$)(CH$_2$CH$_3$), and the like.

"Alkylamino" means mono-alkylamino or di-alkylamino as defined above, such as —NH(alkyl), wherein each alkyl is independently an alkyl group as defined above, including —NHCH$_3$, —NHCH$_2$CH$_3$, —NH(CH$_2$)$_2$CH$_3$, —NH(CH$_2$)$_3$CH$_3$, —NH(CH$_2$)$_4$CH$_3$, —NH(CH$_2$)$_5$CH$_3$, and —N(alkyl)(alkyl), wherein each alkyl is independently an alkyl group as defined above, including —N(CH$_3$)$_2$, —N(CH$_2$CH$_3$)$_2$, —N((CH$_2$)$_2$CH$_3$)$_2$, —N(CH$_3$)(CH$_2$CH$_3$) and the like.

"Carboxyl" and "carboxy" mean —COOH.

"Aminoalkyl" means -(alkyl)-NH$_2$, wherein alkyl is defined above, including CH$_2$—NH$_2$, —(CH$_2$)$_2$—NH$_2$, —(CH$_2$)$_3$—NH$_2$, —(CH$_2$)$_4$—NH$_2$, —(CH$_2$)$_5$—NH$_2$ and the like.

"Mono-alkylaminoalkyl" means -(alkyl)-NH(alkyl), wherein each alkyl is independently an alkyl group defined above, including —CH$_2$—NH—CH$_3$, —CH$_2$—NHCH$_2$CH$_3$, —CH$_2$—NH(CH$_2$)$_2$CH$_3$, —CH$_2$—NH(CH$_2$)$_3$CH$_3$, —CH$_2$—NH(CH$_2$)$_4$CH$_3$, —CH$_2$—NH(CH$_2$)$_5$CH$_3$, —(CH$_2$)$_2$—NH—CH$_3$, and the like.

"Di-alkylaminoalkyl" means -(alkyl)-N(alkyl)(alkyl), wherein each alkyl is independently an alkyl group defined above, including —CH$_2$—N(CH$_3$)$_2$, —CH$_2$—N(CH$_2$CH$_3$)$_2$, —CH$_2$—N((CH$_2$)$_2$CH$_3$)$_2$, —CH$_2$—N(CH$_3$)(CH$_2$CH$_3$), —(CH$_2$)$_2$—N(CH$_3$)$_2$, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, thietanyl and oxazolyl.

"Heterocycle" means a 5- to 7-membered monocyclic, or 7- to 10-membered bicyclic, heterocyclic ring which is either saturated, unsaturated, and which contains from 1 to 4 heteroatoms independently selected from nitrogen, oxygen and sulfur, and wherein the nitrogen and sulfur heteroatoms can be optionally oxidized, and the nitrogen heteroatom can be optionally quaternized, including bicyclic rings in which any of the above heterocycles are fused to a benzene ring. The heterocycle can be attached via any heteroatom or carbon atom. Heterocycles include heteroaryls as defined above. Representative heterocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocycle fused to phenyl" means a heterocycle, wherein heterocycle is defined as above, that is attached to a phenyl ring at two adjacent carbon atoms of the phenyl ring.

"Haloalkyl" means alkyl, wherein alkyl is defined as above, having one or more hydrogen atoms replaced with halogen, wherein halogen is as defined above, including —CF$_3$, —CHF$_2$, —CH$_2$F, —CBr$_3$, —CHBr$_2$, —CH$_2$Br, —CCl$_3$, —CHCl$_2$, —CH$_2$Cl, —CI$_3$, —CHI$_2$, —CH$_2$I, —CH$_2$—CF$_3$, —CH$_2$—CHF$_2$, —CH$_2$—CH$_2$F, —CH$_2$—CBr$_3$, —CH$_2$—CHBr$_2$, —CH$_2$—CH$_2$Br, —CH$_2$—CCl$_3$, —CH$_2$—CHCl$_2$, —CH$_2$—CH$_2$Cl, —CH$_2$—CI$_3$, —CH$_2$—CHI$_2$, —CH$_2$—CH$_2$I, and the like.

"Hydroxyalkyl" means alkyl, wherein alkyl is as defined above, having one or more hydrogen atoms replaced with hydroxy, including —CH$_2$OH, —CH$_2$CH$_2$OH, —(CH$_2$)$_2$CH$_2$OH, —(CH$_2$)$_3$CH$_2$OH, —(CH$_2$)$_4$CH$_2$OH, —(CH$_2$)$_5$CH$_2$OH, —CH(OH)—CH$_3$, —CH$_2$CH(OH)CH$_3$, and the like.

"Hydroxy" means —OH.

"Sulfonyl" means —SO$_3$H.

"Sulfonylalkyl" means —SO$_2$-(alkyl), wherein alkyl is defined above, including —SO$_2$—CH$_3$, —SO$_2$—CH$_2$CH$_3$, —SO$_2$—(CH$_2$)$_2$CH$_3$, —SO$_2$—(CH$_2$)$_3$CH$_3$, —SO$_2$—(CH$_2$)$_4$CH$_3$, —SO$_2$—(CH$_2$)$_5$CH$_3$, and the like.

"Sulfinylalkyl" means —SO-(alkyl), wherein alkyl is defined above, including —SO—CH$_3$, —SO—CH$_2$CH$_3$, —SO—(CH$_2$)$_2$CH$_3$, —SO—(CH$_2$)$_3$CH$_3$, —SO—(CH$_2$)$_4$CH$_3$, —SO—(CH$_2$)$_5$CH$_3$, and the like.

"Thioalkyl" means —S-(alkyl), wherein alkyl is defined above, including —S—CH$_3$, —S—CH$_2$CH$_3$, —S—(CH$_2$)$_2$CH$_3$, —S—(CH$_2$)$_3$CH$_3$, —S—(CH$_2$)$_4$CH$_3$, —S—(CH$_2$)$_5$CH$_3$, and the like.

The term "substituted" as used herein means any of the above groups (i.e., aryl, heteroaryl, heterocycle or cycloalkyl) wherein at least one hydrogen atom of the moiety being substituted is replaced with a substituent. In one embodiment, each carbon atom of the group being substituted is substituted with no more that two substituents. In another embodiment, each carbon atom of the group being substituted is substituted with no more than one substituent. In the case of a keto substituent, two hydrogen atoms are replaced with an oxygen which is attached to the carbon via a double bond. Substituents include halogen, hydroxyl, alkyl, haloalkyl, mono- or di-substituted alkylamino, aryl, heterocycle, —NR$_a$R$_b$, —NR$_a$C(=O)R$_b$, —NR$_a$C(=O)NR$_a$R$_b$, —NR$_a$C(=O)OR$_b$, —NR$_a$SO$_2$R$_b$, —OR$_a$, —C(=O)R$_a$C(=O)OR$_a$—C(=O)NR$_a$R$_b$, —OC(=O)R$_a$, —OC(=O)OR$_a$, —OC(=O)NR$_a$R$_b$, —NR$_a$SO$_2$R$_b$, wherein R$_a$ and R$_b$ are the same or different and independently hydrogen, amino, alkyl, haloalkyl, aryl or heterocycle, or wherein $R_a$ and $R_b$ taken together with the nitrogen atom to which they are attached form a heterocycle.

As used herein, an "effective amount" includes that amount of a Compound of the Invention sufficient to destroy, modify, control or remove a primary, regional or metastatic cancer cell or tissue; delay or minimize the spread of cancer; or provide a therapeutic benefit in the treatment or management of cancer, a neoplastic disorder, acute or chronic renal failure, an inflammatory disorder, an immune disorder, a cardiovascular disease, an effect of aging or an infectious disease. An "effective amount" also includes the amount of a Compound of the Invention sufficient to result in cancer or neoplastic cell death. An "effective amount" also includes the amount of a Compound of the Invention sufficient to modulate (e.g., activate or inhibit, preferably inhibit) ligase activity either in vitro or in vivo.

As used herein, "modulation of ligase activity" means the inhibition, activation or retardation, preferably inhibition, of the rate of activity or the increase of the rate of activity of one or more proteins having ligase activity. In one embodiment, "modulation of ligase activity" means to inhibit the rate of activity of one or more proteins with ligase activity. In another embodiment, "modulation of ligase activity" means the modulation of the ligase complex (e.g., p27/Kip1 complex). In another embodiment, "modulation of ligase activity" means the modulation of one or more proteins in the ligase complex. In another embodiment, "modulation of ligase activity" means the activation one or more proteins having ligase activity. In another embodiment, "modulation of ligase activity" means the retardation of the rate of activity of one or more proteins having ligase activity. In another embodiment, "modulation of ligase activity" means increasing the rate of activity of one or more proteins having ligase activity. The modulation of the ligase activity can be achieved on the mRNA level, protein expression level and kinase activity level.

As used herein, "responsive to modulation of ligase activity" means that the activity of one or more proteins having ligase activity is inhibited or activated, preferably inhibited, by a Compound of the Invention.

As used herein, "modulation of E3 ubiquitin-protein ligase activity" means that the activity of an E3 ubiquitin-protein ligase is inhibited or activated, preferably inhibited by a Compound of the Invention.

As used herein, "modulation of p27/Kip1 levels" means that the amount of p27/Kip1 in a cell contacted with a Compound of the Invention is increased or decreased, preferably increased, relative to a cell that has not been contacted with a Compound of the Invention.

As used herein, a "prophylactically effective amount" refers to that amount of a Compound of the Invention sufficient to result in the prevention of the recurrence or spread of cancer. A prophylactically effective amount can refer to the amount of a Compound of the Invention sufficient to prevent the recurrence or spread of cancer or the occurrence of cancer in a patient, including but not limited to those predisposed to cancer or previously exposed to a carcinogen. A prophylactically effective amount can also refer to the amount of the Compound of the Invention that provides a prophylactic benefit in the prevention of cancer. Further, a prophylactically effective amount with respect to a another prophylactic agent means that amount of that prophylactic agent in combination with a Compound of the Invention that provides a prophylactic benefit in the prevention of cancer. Used in connection with an amount of a Compound of the Invention, the term "prophylactically effective amount" can encompass an amount that improves overall prophylaxis or enhances the prophylactic efficacy of or provides a synergistic affect with another prophylactic agent.

As used herein, the term "neoplastic" means an abnormal growth of a cell or tissue (e.g., a tumor) which may be benign or cancerous.

As used herein, the term "management" includes the provision of one or more beneficial effects that a patient derives from a Compound of the Invention which, in one embodiment, does not cure the disease. In certain embodiments, a patient is administered a Compound of the Invention to "manage" a disease so as to prevent the progression or worsening of the disease.

As used herein, the term "prevention" includes the prevention of the recurrence, spread or onset of cancer in a patient.

As used herein, the term "treatment" includes the eradication, removal, modification, or control of primary, regional, or metastatic cancer tissue; and the minimizing or delay of the spread of cancer.

As used herein, the phrase "Compound(s) of the Invention" includes any compound(s) of Formula (I), Formula (II), Formula (III) (including specific embodiments of each of the compounds of Formulas (I)–(III)), as well as clathrates, hydrates, solvates, polymorphs or pharmaceutically acceptable salts thereof. In one embodiment, the Compounds of the Invention include stereochemically pure compounds, e.g., those substantially free (e.g., greater than 85% ee, greater than 90% ee, greater than 95% ee, greater than 97% ee, or greater than 99% ee) of other stereoisomers.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts for the compound of the present invention include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences,* $18^{th}$ eds., Mack Publishing, Easton Pa. (1990) or *Remington: The Science and Practice of Pharmacy,* $19^{th}$ eds., Mack Publishing, Easton Pa. (1995).

As used herein and unless otherwise indicated, the term "polymorph" refers to solid crystalline forms of a Compound of the Invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "solvate" means a Compound of the Invention or a salt thereof, that further includes a stoichiometric or non-stoichiometric amount of a solvent bound by non-covalent intermolecular forces. Preferred solvents are volatile, non-toxic, and/or acceptable for administration to humans in trace amounts.

As used herein, the term "hydrate" means a Compound of the Invention or a salt thereof, that further includes a stoichiometric or non-stoichiometric amount of water bound by non-covalent intermolecular forces.

As used herein, he term "clathrate" means a Compound of the Invention or a salt thereof in the form of a crystal lattice that contains spaces (e.g., channels) that have a guest molecule (e.g., a solvent or water) trapped within.

As used herein and unless otherwise indicated, the term "prodrug" means a Compound of the Invention that can hydrolyze, oxidize, or otherwise react under biological conditions (in vitro or in vivo) to provide an active compound, particularly a Compound of the Invention. Examples of prodrugs include, but are not limited to, metabolites of a Compound of the Invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6$^{th}$ ed. (Donald J. Abraham ed., 2001, Wiley) and *Design and Application of Prodrugs* (H. Bundgaard ed., 1985, Harwood Academic Publishers Gmfh).

In one embodiment, when administered to a patient, e.g., a mammal for veterinary use or a human for clinical use, the Compound of the Invention is administered in isolated form. As used herein, "isolated" means that the Compound of the Invention is separated from other components of either (a) a natural source, such as a plant, cell or bacterial culture, or (b) a synthetic organic chemical reaction mixture. Preferably, via conventional techniques, the Compound of the Invention is purified. As used herein, "purified" means that when isolated, the isolate is greater than 90% pure, in one embodiment greater than 95% pure, in another embodiment greater than 99% pure and in another embodiment greater than 99.9% pure.

4.2. Compounds of the Invention

As stated above, the present invention relates to Compounds of the Invention such as Compounds of Formula (I):

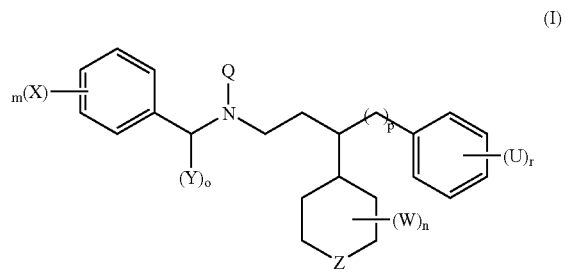

wherein:

X, W and U are at each occurrence independently H, halogen, hydroxy, carboxy, alkoxy, alkylamino, branched or unbranched $C_1$–$C_{10}$ alkyl, $C_2$–$C_{10}$ alkenyl, $C_2$–$C_{10}$ alkynyl, haloalkyl, acyloxy, thioalkyl, sulfonyl, sulfinylalkyl, sulfonylalkyl, hydroxyalkyl, substituted or unsubstituted aryl, substituted or unsubstituted heteroaryl, substituted or unsubstituted heterocycle, substituted or unsubstituted cycloalkyl, —C(=O)OR$_1$, —OC(=O)R$_1$, —C(=O)NR$_1$R$_2$, —C(=O)NR$_1$OR$_2$, —SO$_2$NR$_1$R$_2$, —NR$_1$SO$_2$R$_2$, —CN, —NO$_2$, —NR$_1$R$_2$, —NR$_1$C(=O)R$_2$, —NR$_1$C(=O)(CH$_2$)$_q$OR$_2$, —NR$_1$C(=O)(CH$_2$)$_q$R$_2$, NR$_1$C(=O)(CH$_2$)$_q$NR$_1$R$_2$, —O(CH$_2$)$_q$NR$_1$R$_2$;

R$_1$ and R$_2$ are independently H or branched or unbranched $C_1$–$C_{10}$ alkyl;

Y at each occurrence is independently H, branched or unbranched $C_1$–$C_{10}$ alkyl, or when o is 1, Y can be (=O);

Z is C or O;

Q is H, branched or unbranched $C_1$–$C_{10}$ alkyl;

m is 0–5;

n is 0–8;

o is 0–2;

p is 0–2;

q is 0–5; and r is 0–5;

and prodrugs, clathrates, hydrates, solvates, polymorphs and pharmaceutically acceptable salts thereof.

In one embodiment, the Compounds of Formula (I) do not include (4-{[3-(2,2-Dimethyl-tetrahydro-pyran-4-yl)-4-phenyl-butylamino]-methyl}-phenyl)-dimethyl-amine).

In another embodiment, the Compounds of Formula (I) are those wherein Z is O.

In another embodiment, the Compounds of Formula (I) are those wherein Q is H.

In another embodiment, p is 1 or 2. In a further embodiment, p is 2.

In another embodiment, the Compounds of Formula (I) are those wherein both carbons α to Z are unsubstituted. In a further embodiment, the Compounds of Formula (I) are those wherein both carbons a to Z are substituted. In a further embodiment, the Compounds of Formula (I) are those wherein both carbons α to Z are di-substituted. In a further embodiment, the Compounds of Formula (I) are those wherein both carbons α to Z are mono-substituted. In a further embodiment, the Compounds of Formula (I) are those wherein one carbon α to Z is di-substituted and the other carbon α to Z is mono-substituted.

In another embodiment, W is H, halogen, hydroxy, carboxy, alkoxy, alkylamino, $C_2$–$C_{10}$ alkenyl, $C_2$–$C_{10}$ alkynyl, haloalkyl, acyloxy, thioalkyl, sulfonyl, sulfinylalkyl, sulfonylalkyl, hydroxyalkyl, substituted or unsubstituted aryl, substituted or unsubstituted heteroaryl, substituted or unsubstituted heterocycle, substituted or unsubstituted cycloalkyl, —C(=O)OR$_1$, —OC(=O)R$_1$, —C(=O)NR$_1$R$_2$, —C(=O)NR$_1$OR$_2$, —SO$_2$NR$_1$R$_2$, —NR$_1$SO$_2$R$_2$, —CN, —NO$_2$, —NR$_1$R$_2$, —NR$_1$C(=O)R$_2$, —NR$_1$C(=O)(CH$_2$)$_q$OR$_2$, —NR$_1$C(=O)(CH$_2$)$_q$R$_2$, NR$_1$C(=O)(CH$_2$)$_q$NR$_1$R$_2$ or —O(CH$_2$)$_q$NR$_1$R$_2$.

In another embodiment, U and X are H, halogen, hydroxy, carboxy, alkylamino, branched or unbranched C$_1$–C$_{10}$ alkyl, C$_2$–C$_{10}$ alkenyl, C$_2$–C$_{10}$ alkynyl, haloalkyl, acyloxy, thioalkyl, sulfonyl, sulfinylalkyl, sulfonylalkyl, hydroxyalkyl, substituted or unsubstituted aryl, substituted or unsubstituted heteroaryl, substituted or unsubstituted heterocycle, substituted or unsubstituted cycloalkyl, —C(=O)OR$_1$, —OC(=O)R$_1$, —C(=O)NR$_1$R$_2$, —C(=O)NR$_1$OR$_2$, —SO$_2$NR$_1$R$_2$, —NR$_1$SO$_2$R$_2$, —CN, —NO$_2$, —NR$_1$R$_2$, —NR$_1$C(=O)R$_2$, —NR$_1$C(=O)(CH$_2$)$_q$OR$_2$, —NR$_1$C(=O)(CH$_2$)$_q$R$_2$, NR$_1$C(=O)(CH$_2$)$_q$NR$_1$R$_2$ or —O(CH$_2$)$_q$NR$_1$R$_2$.

In another embodiment, the invention relates to Compounds of the Invention such as Compounds of Formula (II):

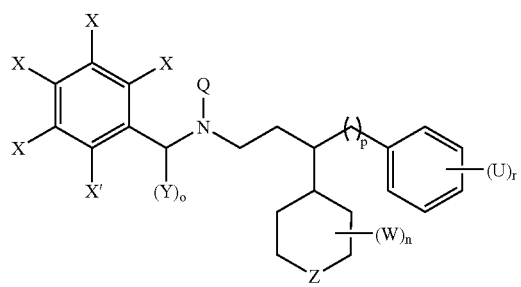

(II)

wherein:
X, W and U are at each occurrence independently H, halogen, hydroxy, carboxy, alkoxy, alkylamino, branched or unbranched C$_1$–C$_{10}$ alkyl, C$_2$–C$_{10}$ alkenyl, C$_2$–C$_{10}$ alkynyl, haloalkyl, acyloxy, thioalkyl, sulfonyl, sulfinylalkyl, sulfonylalkyl, hydroxyalkyl, substituted or unsubstituted aryl, substituted or unsubstituted heteroaryl, substituted or unsubstituted heterocycle, substituted or unsubstituted cycloalkyl, —C(=O)OR$_1$, —OC(=O)R$_1$, —C(=O)NR$_1$R$_2$, —C(=O)NR$_1$OR$_2$, —SO$_2$NR$_1$R$_2$, —NR$_1$SO$_2$R$_2$, —CN, —NO$_2$, —NR$_1$R$_2$, —NR$_1$C(=O)R$_2$, —NR$_1$C(=O)(CH$_2$)$_q$OR$_2$—NR$_1$C(=O)(CH$_2$)$_q$R$_2$, NR$_1$C(=O)(CH$_2$)$_q$NR$_1$R$_2$, —O(CH$_2$)$_q$NR$_1$R$_2$;

X' is H, hydroxy, carboxy, alkoxy, alkylamino, branched or unbranched C$_1$–C$_{10}$ alkyl, C$_2$–C$_{10}$ alkenyl, C$_2$–C$_{10}$ alkynyl, haloalkyl, acyloxy, thioalkyl, sulfonyl, sulfinylalkyl, sulfonylalkyl, hydroxyalkyl, substituted or unsubstituted aryl, substituted or unsubstituted heteroaryl, substituted or unsubstituted heterocycle, substituted or unsubstituted cycloalkyl, —C(=O)OR$_1$, —OC(=O)R$_1$, —C(=O)NR$_1$R$_2$, —C(=O)NR$_1$OR$_2$, —SO$_2$NR$_1$R$_2$, —NR$_1$SO$_2$R$_2$, —CN, —NO$_2$, —NR$_1$R$_2$, —NR$_1$C(=O)R$_2$, —NR$_1$C(=O)(CH$_2$)$_q$OR$_2$, —NR$_1$C(=O)(CH$_2$)$_q$R$_2$, NR$_1$C(=O)(CH$_2$)$_q$NR$_1$R$_2$, —O(CH$_2$)$_q$NR$_1$R$_2$;

R$_1$ and R$_2$ are independently H or branched or unbranched C$_1$–C$_{10}$ alkyl;

Y at each occurrence is independently H, branched or unbranched C$_1$–C$_{10}$ alkyl, or when o is 1, Y can be (=O);
Z is C or O;
Q is H, branched or unbranched C$_1$–C$_{10}$ alkyl;
n is 0–8;
o is 0–2;
p is 0–2;
q is 0–5; and
r is 0–5;

and prodrugs, clathrates, hydrates, solvates, polymorphs and pharmaceutically acceptable salts thereof.

In one embodiment, the Compounds of Formula (II) do not include (4-{[3-(2,2-Dimethyl-tetrahydro-pyran-4-yl)-4-phenyl-butylamino]-methyl}-phenyl)-dimethyl-amine).

In another embodiment, the Compounds of Formula (II) are those wherein Z is O.

In another embodiment, the Compounds of Formula (II) are those wherein Q is H.

In another embodiment, the Compounds of Formula (II) are those wherein one of X, X', U or W is not H.

In another embodiment, the Compounds of Formula (II) are those wherein both carbons α to Z are unsubstituted. In a further embodiment, the Compounds of Formula (II) are those wherein both carbons α to Z are substituted. In a further embodiment, the Compounds of Formula (II) are those wherein both carbons α to Z are di-substituted. In a further embodiment, the Compounds of Formula (II) are those wherein both carbons α to Z are mono-substituted. In a further embodiment, the Compounds of Formula (II) are those wherein one carbon α to Z is di-substituted and the other carbon α to Z is mono-substituted.

In another embodiment, the invention relates to Compounds of the Invention such as Compounds of Formula (III):

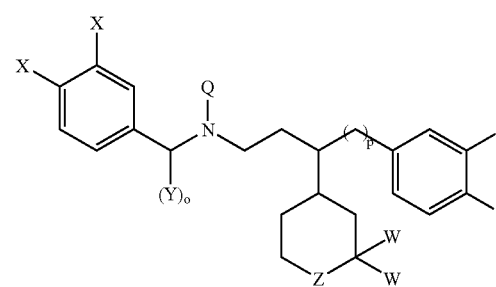

(III)

X, W and U are at each occurrence independently H, halogen, hydroxy, carboxy, alkoxy, alkylamino, branched or unbranched C$_1$–C$_{10}$ alkyl, C$_2$–C$_{10}$ alkenyl, C$_2$–C$_{10}$ alkynyl, haloalkyl, acyloxy, thioalkyl, sulfonyl, sulfinylalkyl, sulfonylalkyl, hydroxyalkyl, substituted or unsubstituted aryl, substituted or unsubstituted heteroaryl, substituted or unsubstituted heterocycle, substituted or unsubstituted cycloalkyl, —C(=O)OR$_1$, —OC(=O)R$_1$, —C(=O)NR$_1$R$_2$, —C(=O)NR$_1$OR$_2$, —SO$_2$NR$_1$R$_2$, —NR$_1$SO$_2$R$_2$, —CN, —NO$_2$, —NR$_1$R$_2$, —NR$_1$C(=O)R$_2$, —NR$_1$C(=O)(CH$_2$)$_q$OR$_2$, —NR$_1$C(=O)(CH$_2$)$_q$R$_2$, NR$_1$C(=O)(CH$_2$)$_q$NR$_1$R$_2$, —O(CH$_2$)$_q$NR$_1$R$_2$;

R$_1$ and R$_2$ are independently H or branched or unbranched C$_1$–C$_{10}$ alkyl;

Y at each occurrence is independently H, branched or unbranched C$_1$–C$_{10}$ alkyl, or when o is 1, Y can be (=O);
Z is C or O;
Q is H, branched or unbranched $C_1$–$C_{10}$ alkyl;
o is 0–2;
p is 0–2; and
q is 0–5;

and prodrugs, clathrates, hydrates, solvates, polymorphs and pharmaceutically acceptable salts thereof.

In one embodiment, the Compounds of Formula (III) do not include (4-{[3-(2,2-Dimethyl-tetrahydro-pyran-4-yl)-4-phenyl-butylamino]-methyl}-phenyl)-dimethyl-amine).

In another embodiment, the Compounds of Formula (III) are those wherein Z is O.

In another embodiment, the Compounds of Formula (III) are those wherein Q is H.

In another embodiment, the Compounds of Formula (III) are those wherein both carbons α to Z are unsubstituted. In a further embodiment, the Compounds of Formula (III) are those wherein both carbons α to Z are substituted. In a further embodiment, the Compounds of Formula (III) are those wherein both carbons α to Z are di-substituted. In a further embodiment, the Compounds of Formula (III) are those wherein both carbons α to Z are mono-substituted. In a further embodiment, the Compounds of Formula (III) are those wherein one carbon α to Z is di-substituted and the other carbon α to Z is mono-substituted.

The present invention also relates to pharmaceutical compositions comprising an effective amount of a Compound of the Invention and a pharmaceutically acceptable carrier. In one embodiment, the pharmaceutical composition is suitable for treating a disease associated with the modulation of a ligase. In another embodiment, the pharmaceutical composition is suitable for treating a disease associated with the inhibitition of a ligase.

The Compound of the Invention and pharmaceutical compositions thereof are useful for modulating ligase activity; treating or preventing a disease responsive to the modulation of ligase activity; treating or preventing a disease responsive to the inhibition of ligase activity; treating or preventing a disease responsive to the activation of ligase activity; modulating E3 ubiquitin-protein ligase activity; modulating E3 ubiquitin-protein ligase mediated ubiquitination of p27/Kip1; modulating cellular p27/Kip1; arresting the growth of a cell; treating or preventing side-effects associated with chemotherapy or radiation therapy; increasing the lifetime of a cell, blood, tissue, an organ or an organism that is cryopreserved; regulating and controlling the differentiation and maturation of mammalian, particularly human stem cells along specific cell and tissue lineages, in particular, to the differentiation of embryonic-like stem cells originating from a postpartum placenta or for the differentiation of stem cells isolated form sources such as cord blood; treating or preventing cancer or neoplastic disease in a patient in need of such treatment or prevention; or inhibiting the growth of a cancer cell or neoplastic cell.

In another embodiment, the invention relates to methods for treating or preventing a disease responsive to the modulation of ligase activity in a patient comprising administering to a patient in need of such treatment or prevention an effective amount of a Compound of the Invention. Diseases responsive to the modulation of ligase activity in a patient include cancer, neoplastic diseases, inflammatory diseases, infectious diseases, cardiovascular diseases and immune diseases.

In another embodiment, the invention relates to methods for treating or preventing a disease responsive to the modulation of the cellular level of p27/Kip1 in a patient comprising administering to a patient in need of such treatment or prevention an effective amount of a Compound of the Invention. Diseases responsive to the modulation of the cellular level of p27/Kip1 in a patient include cancer, neoplastic diseases, inflammatory diseases, infectious diseases, cardiovascular diseases and immune diseases.

In another embodiment, the invention relates to methods for arresting the growth of a cell comprising contacting a cell in need of growth arrestment with an effective amount of a Compound of the Invention.

In another embodiment, the invention relates to methods for causing the death of a cancer or neoplastic cell comprising contacting a cancer or neoplastic cell with an effective amount of a Compound of the Invention.

In another embodiment, the invention relates to methods for treating or preventing a side-effect associated with chemotherapy or radiation therapy, comprising administering to a patient in need of such treatment or prevention an effective amount of a Compound of the Invention. Side-effects associated with chemotherapy or radiation therapy include low blood count, nausea, diarrhea, oral lesions and alopecia (hair loss).

In another embodiment, the invention relates to methods for preserving a cell, blood, tissue an organ or an organism comprising contacting the cell, blood, tissue, organ or organism with an effective amount of a Compound of the Invention.

In another embodiment, the invention relates to methods for regulating or controlling the differentiation or maturation of a mammalian stem cell comprising contacting the cell with an effective amount of a Compound of the Invention.

In another embodiment, the invention relates to methods for treating or preventing cancer or neoplastic disease in a patient comprising administering to a patient in need of such treatment or prevention an effective amount of a Compound of the Invention.

In another embodiment, the invention relates to methods for treating or preventing cancer or neoplastic disease in a patient comprising contacting a cancer or neoplastic cell with an effective amount of a Compound of the Invention.

In another embodiment, the invention relates to methods for inhibiting the growth of a cancer cell or neoplastic cell comprising a contacting a cancer cell or neoplastic cell with an effective amount of a Compound of the Invention.

In another embodiment, the invention relates to methods for treating or preventing acute or chronic renal failure in a patient comprising administering to a patient in need of such treatment an effective amount of a Compound of the Invention.

In another embodiment, the invention relates to methods for treating or preventing an inflammatory disease in a patient comprising administering to a patient in need of such treatment or prevention an effective amount of a Compound of the Invention.

In another embodiment, the invention relates to methods for treating or preventing an effect of aging in a patient comprising administering to a patient in need of such treatment or prevention an effective amount of a Compound of the Invention. Effects of aging include sarcopenia (loss of muscle mass) and loss of memory.

In another embodiment, the invention relates to methods for treating or preventing an infectious disease in a patient comprising administering to a patient in need of such treatment or prevention an effective amount of a Compound of the Invention.

In another embodiment, the invention relates to methods for treating or preventing an immune disorder in a patient comprising administering to a patient in need of such treatment or prevention an effective amount of a Compound of the Invention.

In another embodiment, the invention relates to methods for treating or preventing a cardiovascular disease in a patient comprising administering to a patient in need of such treatment or prevention an effective amount of a Compound of the Invention.

4.3. Preparation of the Compounds of the Invention

The Compounds of the Invention can be prepared using commercially available starting materials and conventional organic reactions and reagents.

The Compounds of the Invention can generally be prepared by one skilled in the art as set forth in Schemes I–III, below.

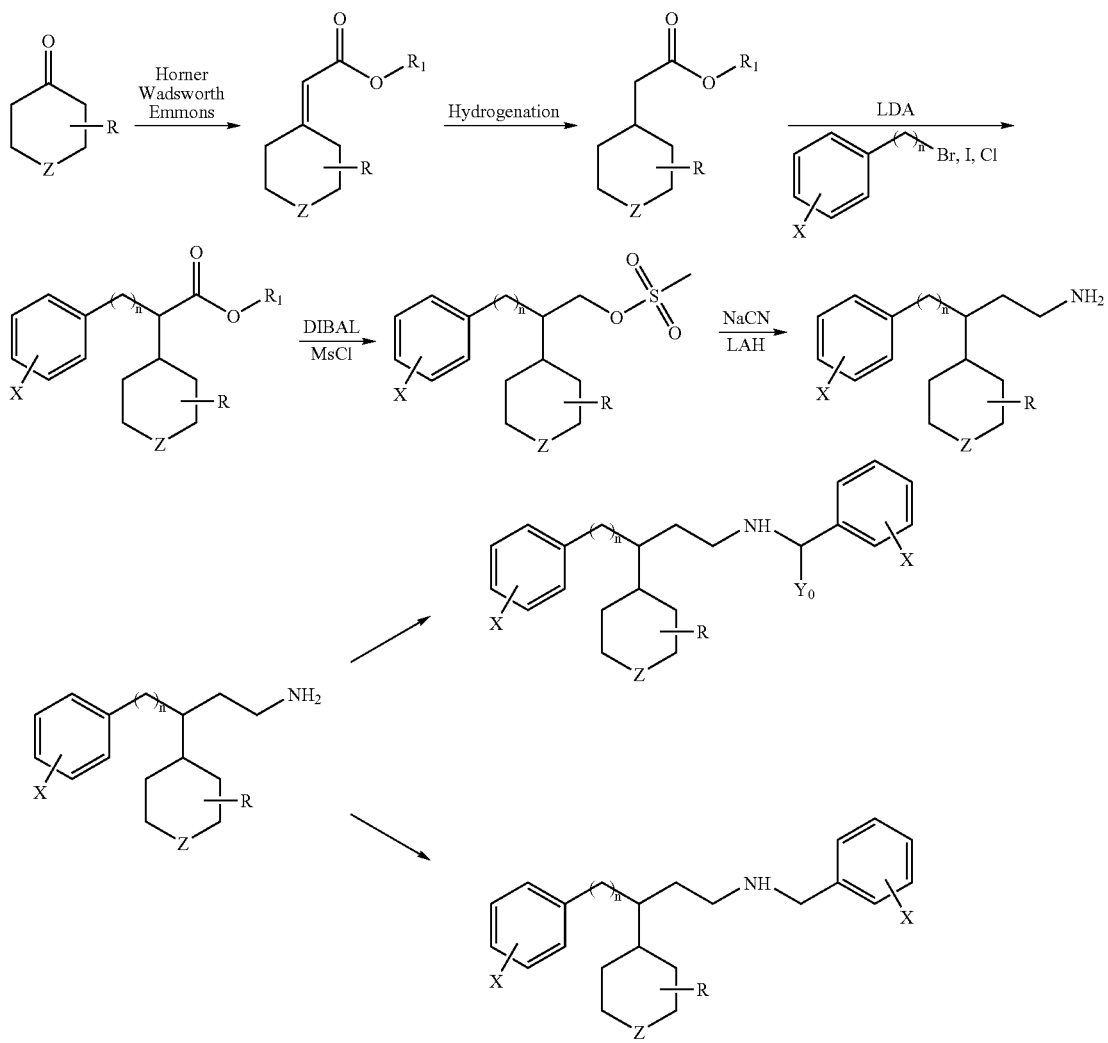

Scheme I

Wherein the variable Z represents carbon or oxygen, the variable $R_1$ represents alkyl, in a specific embodiment lower alkyl (e.g., methyl), and the variables X and R at each occurrence independently represent one or more optional substituents (e.g, halogen, alkyl, haloalkyl, alkoxy, amino, alkylamino, or any other suitable substituent known to one skilled in the art, including those set forth in Section 4.1, above) and the variable n represents an integer ranging from 0–2. One skilled in the art would recognize that minor modifications of Scheme I may be necessary depending on the particular starting materials and reagents used.

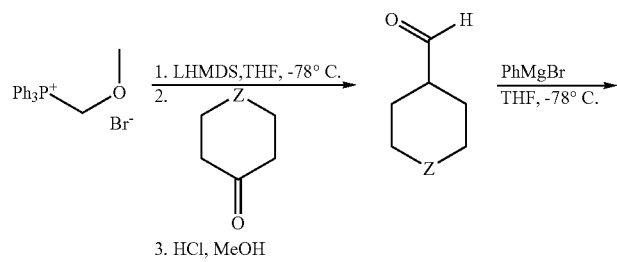
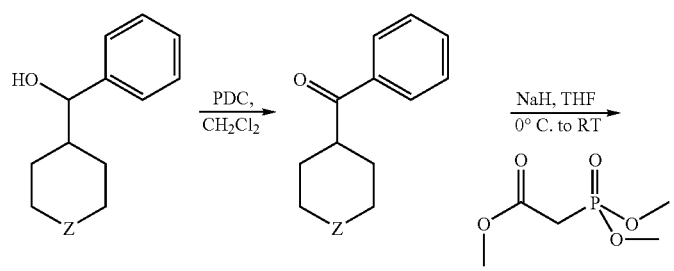
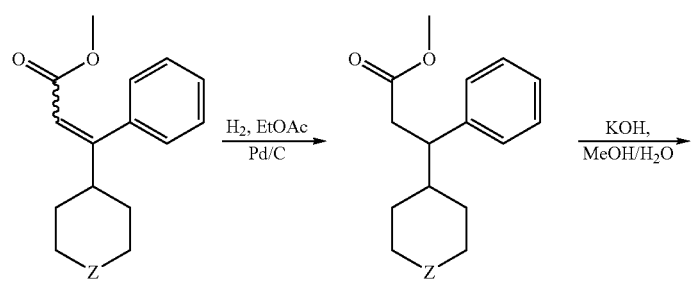
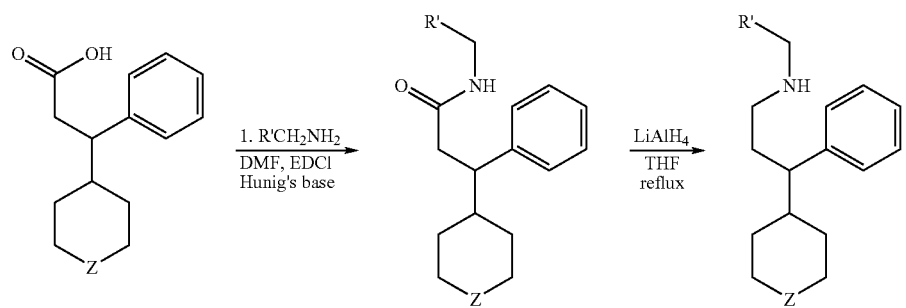

Wherein the variable Z represents carbon or oxygen and the variable R' represents substituted or unsubstituted phenyl.
The compound of EXAMPLE 1 ((4-{[3-(2,2-Dimethyl-tetrahydro-pyran-4-yl)-4-phenyl-butylamino]-methyl}-phenyl)-dimethyl-amine), an illustrative example of the Compounds of the Invention, can be prepared as shown in Scheme III, below:
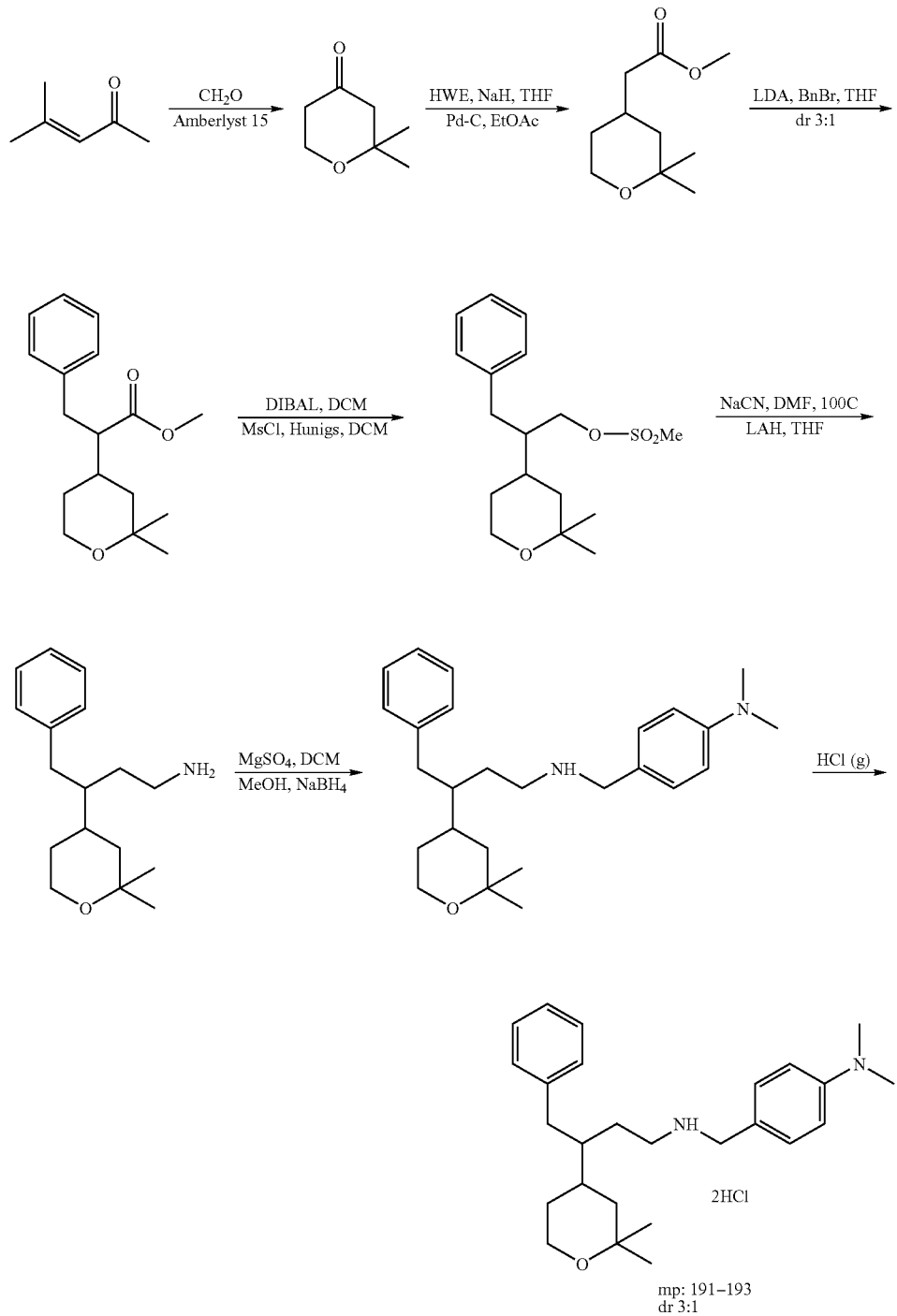

The compound of EXAMPLE 1 can also be obtained commercially from ChemBridge Corporation (16981 Via Tazon, suite G, San Diego, Calif. 92127; catalog no. 5936317). The commercially obtained compound of EXAMPLE 1 shows one peak by HPLC (20–100% gradient: acetonitrile/water/1% trifluoroacetic acid).

4.4. Illustrative Compounds

Illustrative examples of the Compounds of the Invention include:

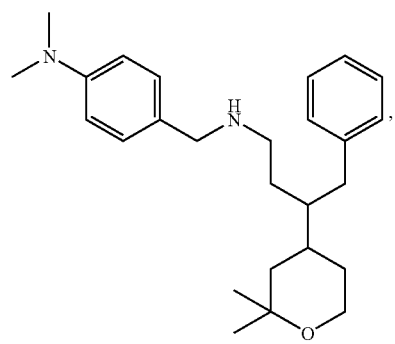

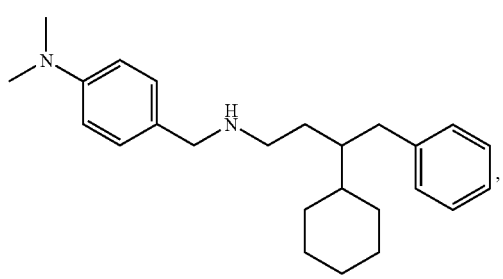

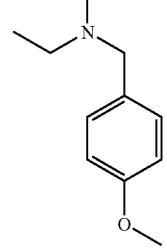

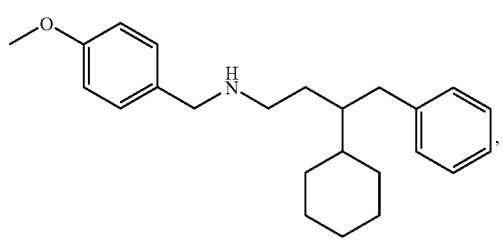

-continued

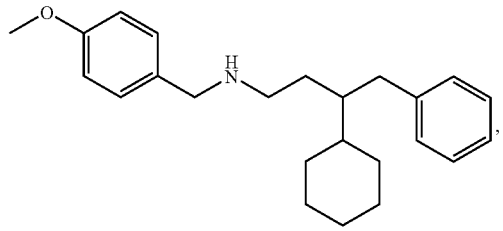

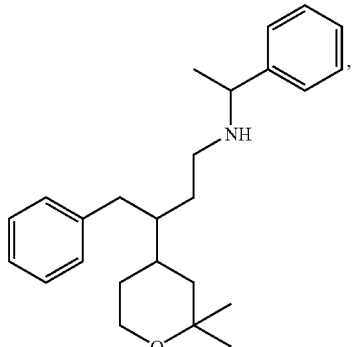

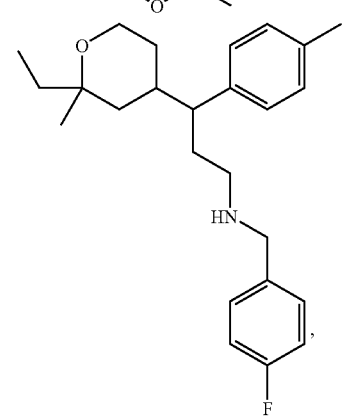

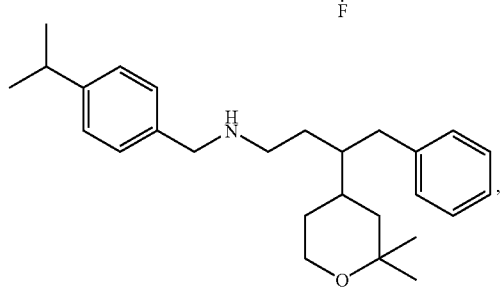

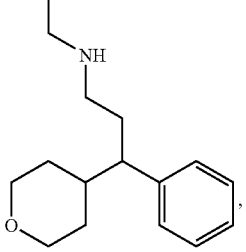

-continued

-continued

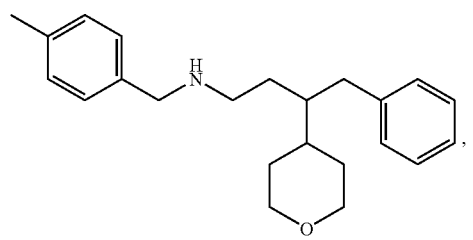

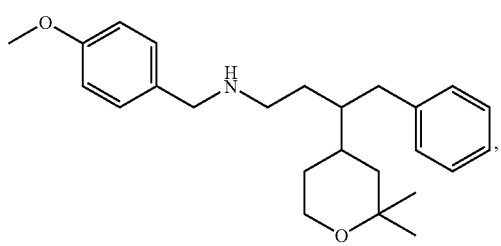

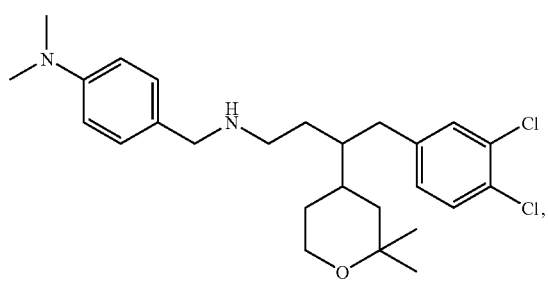

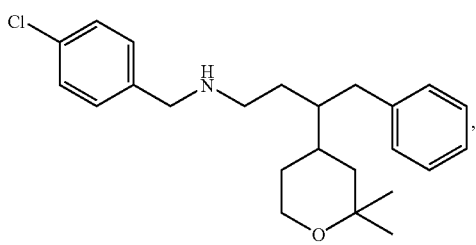

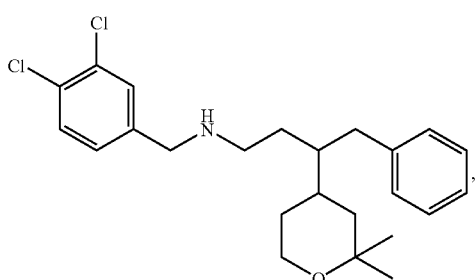

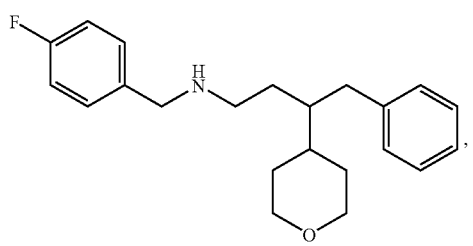

-continued

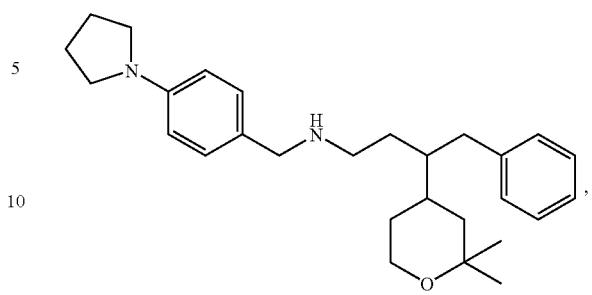

and prodrugs, clathrates, hydrates, solvates, polymorphs and pharmaceutically acceptable salts thereof.

4.5. Therapeutic/Prophylactic Administration and Compositions

The Compounds of the Invention are advantageously useful in veterinary and human medicine. For example, the Compounds of the Invention are useful for the treatment or prevention of cancer, a neoplastic disorder, acute or chronic renal failure, an inflammatory disorder, an immune disorder, a cardiovascular disease, a side-effect of chemotherapy or radiation therapy, an effect of aging or an infectious disease. The Compounds of the Invention are also useful for inhibiting the growth of a cancer cell or neoplastic cell.

The present pharmaceutical compositions, which comprise an effective amount of a Compound of the Invention, can be administered by any convenient route, for example, by infusion or bolus injection, by absorption through epithelial or mucocutaneous linings (e.g., oral mucosa, rectal and intestinal mucosa, etc.) and can be administered together with another therapeutic agent. Administration can be systemic or local. Various delivery systems are known, e.g., encapsulation in liposomes, microparticles, microcapsules or capsules, and can be used to administer a Compound of the Invention. In certain embodiments, more than one Compound of the Invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically to the ears, nose, eyes, or skin. The preferred mode of administration is left to the discretion of the practitioner, and will depend in-part upon the site of the medical condition (such as the site of cancer).

In specific embodiments, it may be desirable to administer one or more Compounds of the Invention locally to the area in need of treatment. This can be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue.

In certain embodiments, it may be desirable to administer one or more Compounds of the Invention using any suitable route, including intraventricular and intrathecal injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Compound of the Invention can be formulated as a suppository, with traditional binders and carriers such as triglycerides.

In another embodiment, the Compound of the Invention can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the Compound of the Invention can be delivered in a controlled-release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled-release system can be placed in proximity of the target of the Compound of the Invention, thus requiring only a fraction of the systemic dose (see, e.g., Goodson, in Medical Applications of Controlled Release, supra, vol. 2, pp. 115–138 (1984)). Other controlled-release systems discussed in the review by Langer (Science 249:1527–1533 (1990)) may be used.

The present pharmaceutical compositions contain an effective amount of a Compound of the Invention, preferably in purified form, together with a suitable amount of a pharmaceutically acceptable carrier so as to provide the form for proper administration to the patient.

In a one embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which a Compound of the Invention is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. In addition, auxiliary, stabilizing, thickening, lubricating and coloring agents may be used. When administered to a patient, Compounds of the Invention are preferably sterile. Water is a preferred carrier when the Compound of the Invention is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable carrier is a capsule (see e.g., U.S. Pat. No. 5,698,155). Other examples of suitable pharmaceutical carriers are described in "Remington's Pharmaceutical Sciences" by E. W. Martin.

In a preferred embodiment, the Compounds of the Invention are formulated in accordance with routine procedures as a pharmaceutical composition adapted for intravenous administration to human beings. Typically, Compounds of the Invention for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the Compound of the Invention is to be administered by infusion, it can be dispensed, for example, with an infusion bottle containing sterile pharmaceutical grade water or saline. Where the Compound of the Invention is administered by injection, an ampoule of sterile water for injection or saline can be provided so that the ingredients may be mixed prior to administration.

Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered Compounds of the Invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard carriers such as mannitol, lactose, starch, magnesium stearate, sodium saccharine, cellulose, magnesium carbonate, etc. Such carriers are preferably of pharmaceutical grade.

The amount of the Compound of the Invention that will be effective in the treatment of a particular disorder or condition will depend on the nature of the disorder or condition, and can be determined by standard clinical techniques. In addition, in vitro or in vivo assays may optionally be employed to help identify optimal dosage ranges. The precise dose will also depend on the route of administration, and the seriousness of the disease or disorder, and should be decided according to the judgment of the practitioner and each patient's circumstances. However, suitable dosage ranges, particularly for intravenous administration, are generally about 20–500 micrograms of a Compound of the Invention per kilogram body weight. In specific preferred embodiments of the invention, the i.v. dose is about 10–40, 30–60, 60–100, or 100–200 micrograms per kilogram body weight. In other embodiments, the i.v. dose is about 75–150, 150–250, 250–375 or 375–500 micrograms per kilogram body weight. Suitable dosage ranges for intranasal administration are generally about 0.01 pg/kg body weight to 1 mg/kg body weight. Suppositories generally contain a Compound of the Invention in the range of about 0.5% to 10% by weight. Oral compositions preferably contain a Compound of the Invention about 10% to 95% by weight of a Compound of the Invention. In specific preferred embodiments of the invention, suitable dose ranges for oral administration are generally about 1–500 micrograms of a Compound of the Invention per kilogram body weight. In specific preferred embodiments, the oral dose is about 1–10, 10–30, 30–90, or 90–150 micrograms per kilogram body weight. In other embodiments, the oral dose is about 150–250, 250–325, 325–450 or 450–1000 micrograms per kilogram body weight. Effective doses may be extrapolated from dose-response curves derived from in vitro or animal model test systems. Such animal models and systems are well known in the art.

The invention also provides pharmaceutical kits comprising a container containing a Compound of the Invention. Optionally associated with such container(s) can be a notice in the form prescribed by a governmental agency regulating the manufacture, use or sale of pharmaceuticals or biological products, which notice reflects approval by the agency of manufacture, use or sale for human administration; or instructions for use. The kit can also comprise a container containing a chemotherapeutic agent useful for treating cancer or a neoplastic disease.

The Compounds of the Invention are preferably assayed in vitro, and then in vivo, for the desired therapeutic or prophylactic activity, prior to use in humans. For example, in vitro assays can be used to determine whether administration of one or more Compounds of the Invention is preferred.

In one embodiment, a patient tissue sample is grown in culture, and contacted or otherwise administered with a Compound of the Invention, and the effect of such Compound of the Invention upon the tissue sample is observed and compared to a non-contacted tissue. In other embodiments, a cell-culture model is used in which the cells of the cell culture are contacted or otherwise administered with a Compound of the Invention, and the effect of such Compound of the Invention upon the cell-culture is observed and compared to a non-contacted cell culture. Generally, a lower level of proliferation or survival of the contacted cells compared to the non-contracted cells indicates that the Compound of the Invention is effective to treat a the patient. Such Compounds of the Invention may also be demonstrated effective and safe using animal model systems.

Other methods will be known to the skilled artisan and are within the scope of the invention.

4.6. Inhibition of Cancer and Neoplastic Cells and Disease

The Compounds of the Invention may be demonstrated to inhibit tumor cell proliferation, cell transformation and tumorigenesis in vitro or in vivo using a variety of assays known in the art, or described herein. Such assays can use cells of a cancer cell line or cells from a patient. Many assays well-known in the art can be used to assess such survival and/or growth; for example, cell proliferation can be assayed by measuring ($^3$H)-thymidine incorporation, by direct cell count, by detecting changes in transcription, translation or activity of known genes such as proto-oncogenes (e.g., fos, myc) or cell cycle markers (Rb, cdc2, cyclin A, D1, D2, D3 or E). The levels of such protein and mRNA and activity can be determined by any method well known in the art. For example, protein can be quantitated by known immunodiagnostic methods such as Western blotting or immunoprecipitation using commercially available antibodies (for example, many cell cycle marker antibodies are from Santa Cruz, Inc.). mRNA can be quantitated by methods that are well known and routine in the art, for example by northern analysis, RNase protection, the polymerase chain reaction in connection with the reverse transcription, etc. Cell viability can be assessed by using trypan-blue staining or other cell death or viability markers known in the art. Differentiation can be assessed visually based on changes in morphology, etc.

The present invention provides for cell cycle and cell proliferation analysis by a variety of techniques known in the art, including but not limited to the following:

As one example, bromodeoxyuridine ("BRDU") incorporation may be used as an assay to identify proliferating cells. The BRDU assay identifies a cell population undergoing DNA synthesis by incorporation of BRDU into newly synthesized DNA. Newly synthesized DNA may then be detected using an anti-BRDU antibody (see Hoshino et al., 1986, Int. J. Cancer 38, 369; Campana et al., 1988, J. Immunol. Meth. 107, 79).

Cell proliferation may also be examined using (3H)-thymidine incorporation (see e.g., Chen, J., 1996, Oncogene 13:1395–403; Jeoung, J., 1995, J. Biol. Chem. 270:18367–73). This assay allows for quantitative characterization of S-phase DNA synthesis. In this assay, cells synthesizing DNA will incorporate (3H)-thyrnidine into newly synthesized DNA. Incorporation may then be measured by standard techniques in the art such as by counting of radioisotope in a Scintillation counter (e.g., Beckman LS 3800 Liquid Scintillation Counter).

Detection of proliferating cell nuclear antigen (PCNA) may also be used to measure cell proliferation. PCNA is a 36 kilodalton protein whose expression is elevated in proliferating cells, particularly in early G1 and S phases of the cell cycle and therefore may serve as a marker for proliferating cells. Positive cells are identified by immunostaining using an anti-PCNA antibody (see Li et al., 1996, Curr. Biol. 6:189–199; Vassilev et al., 1995, J. Cell Sci. 108:1205–15).

Cell proliferation may be measured by counting samples of a cell population over time (e.g., daily cell counts). Cells may be counted using a hemacytometer and light microscopy (e.g., HyLite hemacytometer, Hausser Scientific). Cell number may be plotted against time in order to obtain a growth curve for the population of interest. In a preferred embodiment, cells counted by this method are first mixed with the dye Trypan-blue (Sigma), such that living cells exclude the dye, and are counted as viable members of the population.

DNA content and/or mitotic index of the cells may be measured, for example, based on the DNA ploidy value of the cell. For example, cells in the G1 phase of the cell cycle generally contain a 2N DNA ploidy value. Cells in which DNA has been replicated but have not progressed through mitosis (e.g., cells in S-phase) will exhibit a ploidy value higher than 2N and up to 4N DNA content. Ploidy value and cell-cycle kinetics may be further measured using propidum iodide assay (see e.g., Turner, T., et al., 1998, Prostate 34:175–81). Alternatively, the DNA ploidy may be determined by quantitation of DNA Feulgen staining (which binds to DNA in a stoichiometric manner) on a computerized microdensitometrystaining system (see e.g., Bacus, S., 1989, Am. J. Pathol. 135:783–92). In an another embodiment, DNA content may be analyzed by preparation of a chromosomal spread (Zabalou, S., 1994, Hereditas. 120: 127–40; Pardue, 1994, Meth. Cell Biol. 44:333–351).

The expression of cell-cycle proteins (e.g., CycA. CycB, CycE, CycD, cdc2, Cdk4/6, Rb, p21 or p27) provide crucial information relating to the proliferative state of a cell or population of cells. For example, identification in an antiproliferation signaling pathway may be indicated by the induction of p21cip1. Increased levels of p21 expression in cells results in delayed entry into G1 of the cell cycle (Harper et al., 1993, Cell 75:805–816; Li et al., 1996, Curr. Biol. 6:189–199). p21 induction may be identified by immunostaining using a specific anti-p21 antibody available commercially (e.g., from Santa Cruz, Inc.). Similarly, cell-cycle proteins may be examined by Western blot analysis using commercially available antibodies. In another embodiment, cell populations are synchronized prior to detection of a cell cycle protein. Cell-cycle proteins may also be detected by FACS (fluorescence-activated cell sorter) analysis using antibodies against the protein of interest.

Detection of changes in length of the cell cycle or speed of cell cycle may also be used to measure inhibition of cell proliferation by a Compound of the Invention. In one embodiment the length of the cell cycle is determined by the doubling time of a population of cells (e.g., using cells contacted or not contacted with one or more Compounds of the Invention). In another embodiment, FACS analysis is used to analyze the phase of cell cycle progression, or purify G1, S, and G2/M fractions (see e.g., Delia, D. et al., 1997, Oncogene 14:2137–47).

Lapse of cell cycle checkpoint(s), and/or induction of cell cycle checkpoint(s), may be examined by the methods described herein, or by any method known in the art. Without limitation, a cell cycle checkpoint is a mechanism which ensures that a certain cellular events occur in a particular order. Checkpoint genes are defined by mutations that allow late events to occur without prior completion of an early event (Weinert, T., and Hartwell, L., 1993, Genetics, 134:63–80). Induction or inhibition of cell cycle checkpoint genes may be assayed, for example, by Western blot analysis, or by immunostaining, etc. Lapse of cell cycle checkpoints may be further assessed by the progression of a cell through the checkpoint without prior occurrence of specific events (e.g. progression into mitosis without complete replication of the genomic DNA).

In addition to the effects of expression of a particular cell cycle protein, activity and post-translational modifications of proteins involved in the cell cycle can play an integral role in the regulation and proliferative state of a cell. The invention provides for assays involved detected post-translational modifications (e.g., phosphorylation) by any method known in the art. For example, antibodies that detect phosphorylated tyrosine residues are commercially available, and may be used in Western blot analysis to detect proteins with such modifications. In another example, modifications such as myristylation, may be detected on thin layer chromatography or reverse phase h.p.l.c. (see e.g., Glover, C., 1988, Biochem. J. 250:485–91; Paige, L., 1988, Biochem J.; 250:485–91).

Activity of signaling and cell cycle proteins and/or protein complexes is often mediated by a kinase activity. The present invention provides for analysis of kinase activity by assays such as the histone H1 assay (see e.g., Delia, D. et al., 1997, Oncogene 14:2137–47).

The Compounds of the Invention can also be demonstrated to alter cell proliferation in cultured cells in vitro using methods which are well known in the art. Specific examples of cell culture models include, but are not limited to, for lung cancer, primary rat lung tumor cells (Swafford et al., 1997, Mol. Cell. Biol., 17:1366–1374) and large-cell undifferentiated cancer cell lines (Mabry et al., 1991, Cancer Cells, 3:53–58); colorectal cell lines for colon cancer (Park and Gazdar, 1996, J. Cell Biochem. Suppl. 24:131–141); multiple established cell lines for breast cancer (Hambly et al., 1997, Breast Cancer Res. Treat. 43:247–258; Gierthy et al., 1997, Chemosphere 34:1495–1505; Prasad and Church, 1997, Biochem. Biophys. Res. Commun. 232:14–19); a number of well-characterized cell models for prostate cancer (Webber et al., 1996, Prostate, Part 1, 29:386–394; Part 2, 30:58–64; and Part 3, 30:136–142; Boulikas, 1997, Anticancer Res. 17:1471–1505); for genitourinary cancers, continuous human bladder cancer cell lines (Ribeiro et al., 1997, Int. J. Radiat. Biol. 72:11–20); organ cultures of transitional cell carcinomas (Booth et al., 1997, Lab Invest. 76:843–857) and rat progression models (Vet et al., 1997, Biochim. Biophys Acta 1360:39–44); and established cell lines for leukemias and lymphomas (Drexler, 1994, Leuk. Res. 18:919–927, Tohyama, 1997, Int. J. Hematol. 65:309–317).

The Compounds of the Invention can also be demonstrated to inhibit cell transformation (or progression to malignant phenotype) in vitro. In this embodiment, cells with a transformed cell phenotype are contacted with one or more Compounds of the Invention, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see Luria et al., 1978, General Virology, 3d Ed., John Wiley & Sons, New York, pp. 436–446).

Loss of invasiveness or decreased adhesion may also be used to demonstrate the anti-cancer effects of the Compounds of the Invention. For example, a critical aspect of the formation of a metastatic cancer is the ability of a precancerous or cancerous cell to detach from primary site of disease and establish a novel colony of growth at a secondary site. The ability of a cell to invade peripheral sites is reflective of a potential for a cancerous state. Loss of invasiveness may be measured by a variety of techniques known in the art including, for example, induction of E-cadherin-mediated cell—cell adhesion. Such E-cadherin-mediated adhesion can result in phenotypic reversion and loss of invasiveness (Hordijk et al., 1997, Science 278: 1464–66).

Loss of invasiveness may further be examined by inhibition of cell migration. A variety of 2-dimensional and 3-dimensional cellular matrices are commercially available (Calbiochem-Novabiochem Corp. San Diego, Calif.). Cell migration across or into a matrix may be examined by microscopy, time-lapsed photography or videography, or by any method in the art allowing measurement of cellular migration. In a related embodiment, loss of invasiveness is examined by response to hepatocyte growth factor (HGF). HGF-induced cell scattering is correlated with invasiveness of cells such as Madin-Darby canine kidney (MDCK) cells. This assay identifies a cell population that has lost cell scattering activity in response to HGF (Hordijk et al., 1997, Science 278:1464–66).

Alternatively, loss of invasiveness may be measured by cell migration through a chemotaxis chamber (Neuroprobe/Precision Biochemicals Inc. Vancouver, BC). In such assay, a chemo-attractant agent is incubated on one side of the chamber (e.g., the bottom chamber) and cells are plated on a filter separating the opposite side (e.g., the top chamber). In order for cells to pass from the top chamber to the bottom chamber, the cells must actively migrate through small pores in the filter. Checkerboard analysis of the number of cells that have migrated may then be correlated with invasiveness (see e.g., Ohnishi, T., 1993, Biochem. Biophys. Res. Commun. 193:518–25).

The Compounds of the Invention can also be demonstrated to inhibit tumor formation in vivo. A vast number of animal models of hyperproliferative disorders, including tumorigenesis and metastatic spread, are known in the art (see Table 317-1, Chapter 317, "Principals of Neoplasia," in Harrison's Principals of Internal Medicine, 13th Edition, Isselbacher et al., eds., McGraw-Hill, N.Y., p. 1814, and Lovejoy et al., 1997, J. Pathol. 181:130–135). Specific examples include for lung cancer, transplantation of tumor nodules into rats (Wang et al., 1997, Ann. Thorac. Surg. 64:216–219) or establishment of lung cancer metastases in SCID mice depleted of NK cells (Yono and Sone, 1997, Gan To Kagaku Ryoho 24:489–494); for colon cancer, colon cancer transplantation of human colon cancer cells into nude mice (Gutman and Fidler, 1995, World J. Surg. 19:226–234), the cotton top tamarin model of human ulcerative colitis (Warren, 1996, Aliment. Pharmacol. Ther. 10 Supp 12:45–47) and mouse models with mutations of the adenomatous polyposis tumor suppressor (Polakis, 1997, Biochim. Biophys. Acta 1332:F127–F147); for breast cancer, transgenic models of breast cancer (Dankort and Muller, 1996, Cancer Treat. Res. 83:71–88; Amundadittir et al., 1996, Breast Cancer Res. Treat. 39:119–135) and chemical induction of tumors in rats (Russo and Russo, 1996, Breast Cancer Res. Treat. 39:7–20); for prostate cancer, chemically-induced and transgenic rodent models, and human xenograft models (Royai et al., 1996, Semin. Oncol. 23:35–40); for genitourinary cancers, induced bladder neoplasm in rats and mice (Oyasu, 1995, Food Chem. Toxicol 33:747–755) and xenografts of human transitional cell carcinomas into nude rats (Jarrett et al., 1995, J. Endourol. 9:1–7); and for hematopoietic cancers, transplanted allogeneic marrow in animals (Appelbaum, 1997, Leukemia 11 (Suppl. 4):S15–S17). Further, general animal models applicable to many types of cancer have been described, including, but not restricted to, the p53-deficient mouse model (Donehower, 1996, Semin. Cancer Biol. 7:269–278), the Min mouse (Shoemaker et al., 1997, Biochem. Biophys. Acta, 1332:F25–F48), and immune responses to tumors in rat (Frey, 1997, Methods, 12:173–188).

For example, a Compound of the Invention can be administered to a test animal, in one embodiment a test animal predisposed to develop a type of tumor, and the test animal subsequently examined for an decreased incidence of tumor formation in comparison with an animal not administered the Compound of the Invention. Alternatively, a Compound of the Invention can be administered to test animals having tumors (e.g., animals in which tumors have been induced by introduction of malignant, neoplastic, or transformed cells, or by administration of a carcinogen) and subsequently examining the tumors in the test animals for tumor regression in comparison to animals not administered the Compound of the Invention.

4.7. In Vitro Inhibition of Ubiouitination of p27

The Compounds of the Invention may be demonstrated to inhibit the ubiquitination of p27 in vitro using assays known in the art, or described herein. An exemplary in vitro assay is described by Alessandrini et al. ((1997) Leukemia 11:342–345) wherein a purified recombinant hexahistidine-tagged p27 (p27-his$_6$) is used as a substrate for ubiquitination, and rabbit reticulocyte lysate (RRL) is used as a source of ubiquitinating enzymes and proteasome complexes. The extent of ubiquitination with and without the inhibitor can be compared to determine the potency of the inhibitor.

A further exemplary in vitro ubiquitination assay is described in Chiaur et al. PCT International Publication No. WO 00/12679, which is incorporated by reference herein in its entirety. Logarithmically growing KeLa-S3 cells were collected at a density of $6 \times 10^5$ cells/ml. Cells were arrested in G1 phase by 48-hour treatment with 70 mM lovastatin. 1 ml of in vitro translated [$^{35}$S]p27 was incubated at 30° C. for different times (0–75 minutes) in 10 ml of ubiquitination mix containg: 40 mM Tris pH 7.6, 5 mM MgCl$_2$, 1 mM DTT, 10% glycerol, 1 mM ubiquitin aldehyde, 1 mg/ml methyl ubiquitin, 10 mM creatine phosphate, 0.1 mg/ml creatine phosphokinase, 0.5 mM ATP, 1 mM okadaic acid, 20–30 mg HeLa cell extract. Ubiquitin aldehyde can be added to the ubiquitination reaction to inhibit the isopeptidases that would remove the chains of ubiquitin from p27. Addition of methyl ubiquitin competes with the ubiquitin present in the cellular extracts and terminated p27 ubiquitin chains. Such chains appear as discrete bands instead of a high molecular smear. These shorter polyubiquitin chains have lower affinity for the proteasome and therefore are more stable. Reactions are terminated with Laemmli sampler buffer containing b-mercaptoethanol and the products can be analyzed on protein gels under denaturing conditions. Polyubiquitinated p27 forms are identified by autoradiography.

4.8 Treatment or Prevention of Cancer or a Neoplastic Disease in Combination with Chemotherapy or Radiotherapy Cancer or a neoplastic disease, including, but not limited to, a neoplasm, a tumor, a metastasis, or any disease or disorder characterized by uncontrolled cell growth, can be treated or prevented by administration of an effective amount of a Compound of the Invention. In one embodiment, a composition comprising an effective amount of one or more Compounds of the Invention, or a pharmaceutically acceptable salt thereof, is administered.

In certain embodiments, the invention encompasses methods for treating or preventing cancer or a neoplastic disease comprising administering to a patient need thereof an effective amount of a Compound of the Invention and another therapeutic agent. In one embodiment, the therapeutic agent is a chemotherapeutic agent including, but not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In one embodiment, the Compound of the Invention exerts its activity at the same time the other therapeutic agent exerts its activity. Other therapeutic agents are listed in Table 1.

TABLE 1

CHEMOTHERAPEUTICS AND OTHER ANTI-CANCER AGENTS

| | |
|---|---|
| Radiation: | γ-radiation |
| Alkylating agents | |
| Nitrogen mustards: | cyclophosphamide |
| | Ifosfamide |
| | trofosfamide |
| | Chlorambucil |
| Nitrosoureas: | carmustine (BCNU) |
| | Lomustine (CCNU) |
| Alkylsulphonates | busulfan |
| | Treosulfan |
| Triazenes: | Dacarbazine |
| Platinum containing compounds: | Cisplatin |
| | carboplatin |
| Plant Alkaloids | |
| Vinca alkaloids: | vincristine |
| | Vinblastine |
| | Vindesine |
| | Vinorelbine |
| Taxoids: | paclitaxel |
| | Docetaxol |
| DNA Topoisomerase Inhibitors | |
| Epipodophyllins: | etoposide |
| | Teniposide |
| | Topotecan |
| | 9-aminocamptothecin |
| | irinotecan (Campto ®) |
| | crisnatol |
| Mytomycins: | |
| Mytomycin C | Mytomycin C |
| Anti-metabolites | |
| Anti-folates: | |
| DHFR inhibitors: | methotrexate |
| | Trimetrexate |
| IMP dehydrogenase Inhibitors: | mycophenolic acid |
| | Tiazofurin |
| | Ribavirin |
| | EICAR |
| Ribonuclotide reductase Inhibitors: | hydroxyurea |
| | deferoxamine |
| Pyrimidine analogs: | |
| Uracil analogs | 5-Fluorouracil |
| | Floxuridine |
| | Doxifluridine |
| | Ratitrexed |
| Cytosine analogs | cytarabine (ara C) |
| | Cytosine arabinoside |
| | fludarabine |
| Purine analogs: | mercaptopurine |
| | Thioguanine |
| Hormonal therapies | |
| Receptor antagonists: | |
| Anti-estrogens | Tamoxifen |
| | Raloxifene |
| | megestrol |
| LHRH agonists: | goscrclin |
| | Leuprolide acetate |
| Anti-androgens: | flutamide |
| | bicalutamide |
| Retinoids/Deltoids | |
| Vitamin D3 analogs: | EB 1089 |
| | CB 1093 |
| | KH 1060 |
| Photodyamic therapies: | vertoporfin (BPD-MA) |
| | Phthalocyanine |
| | photosensitizer Pc4 |
| | Demethoxy-hypocrellin A |
| | (2BA-2-DMHA) |

TABLE 1-continued

CHEMOTHERAPEUTICS AND OTHER ANTI-CANCER AGENTS

| | |
|---|---|
| Cytokines: | Interferon-α |
| | Interferon-γ |
| | Tumor necrosis factor |
| Others: | |
| Isoprenylation inhibitors: | Lovastatin |
| Dopaminergic neurotoxins: | 1-methyl-4-phenylpyridinium ion |
| Cell cycle inhibitors: | staurosporine |
| Actinomycins: | Actinomycin D |
| | Dactinomycin |
| Bleomycins: | bleomycin A2 |
| | Bleomycin B2 |
| | Peplomycin |
| Anthracyclines: | daunorubicin |
| | Doxorubicin (adriamycin) |
| | Idarubicin |
| | Epirubicin |
| | Pirarubicin |
| | Zorubicin |
| | Mitoxantrone |
| MDR inhibitors: | verapamil |
| $Ca^{2+}$ ATPase inhibitors: | thapsigargin |
| TNF-a inhibitors/ | thalidomide |
| angiogenesis inhibitors | 3-(3,4-dimethoxy-phenyl)-3-(1-oxo-1, |
| | 3-dihydro-isoindol-2-yl)- |
| | propionamide |
| | (SelCIDs ™) |
| | ImiDs ™ |
| | Revimid ™ |
| | Actimid ™ |

In other embodiments, the present methods for treating or preventing cancer further comprise administering radiation therapy. The cancer can be refractory or non-refractory. The Compound of the Invention can be administered to a patient that has undergone surgery as treatment for the cancer.

In a specific embodiment, a Compound of the Invention can be administered to a patient that has undergone surgery as treatment for the cancer concurrently with chemotherapy or radiation therapy. In another specific embodiment, a chemotherapeutic agent or radiation therapy is administered prior or subsequent to administration of a Compound of the Invention, preferably at least an hour, five hours, 12 hours, a day, a week, a month, more preferably several months (e.g., up to three months).

The chemotherapeutic agent or radiation therapy administered concurrently with, or prior or subsequent to, the administration of a Compound of the Invention can be accomplished by any method known in the art. The chemotherapeutic agents are preferably administered in a series of sessions, any one or a combination of the chemotherapeutic agents listed above can be administered. With respect to radiation therapy, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, may also be administered to expose tissues to radiation.

Additionally, the invention provides methods of treatment of cancer or neoplastic disease with a Compound of the Invention as an alternative to chemotherapy or radiation therapy where the chemotherapy or the radiation therapy has proven or may prove too toxic, e.g., results in unacceptable or unbearable side effects, for the patient being treated. The patient being treated can, optionally, be treated with other cancer treatments such as surgery, radiation therapy or chemotherapy, depending on which treatment is found to be acceptable or bearable.

4.9. Cancer and Neoplastic Disease Treatable or Preventable

Cancers or neoplastic diseases and related disorders that can be treated or prevented by administration of a Compound of the Invention include, but are not limited to, cancer of the head, neck, eye, skin, mouth, throat, esophagus, chest, bone, lung, colon, sigmoid, rectum, stomach, prostate, breast, ovary, testicle, kidney, liver, pancreas, brain, intestine, heart or adrenals as well as those listed in Table 2, below (for a review of such disorders, see Fishman et al., 1985, *Medicine,* 2d Ed., J.B. Lippincott Co., Philadelphia):

TABLE 2

| CANCERS AND NEOPLASTIC DISORDERS |
| --- |
| Leukemia |
|     acute leukemia |
|     acute lymphocytic leukemia |
|     acute myelocytic leukemia |
|         myeloblastic |
|         promyelocytic |
|         myelomonocytic |
|         monocytic |
|         erythroleukemia |
|     chronic leukemia |
|     chronic myelocytic (granulocytic) leukemia |
|     chronic lymphocytic leukemia |
| Polycythemia vera |
| Gastric carcinoma |
| Lymphoma (malignant and non-malignant) |
|     Hodgkin's disease |
|     non-Hodgkin's disease |
| Multiple myeloma |
| Waldenström's macroglobulinemia |
| Heavy chain disease |
| Solid tumors |
|     sarcomas and carcinomas |
|         fibrosarcoma |
|         myxosarcoma |
|         liposarcoma |
|         chondrosarcoma |
|         osteogenic sarcoma |
|         chordoma |
|         angiosarcoma |
|         endotheliosarcoma |
|         lymphangiosarcoma |
|         lymphangioendotheliosarcoma |
|         synovioma |
|         mesothelioma |
|         Ewing's tumor |
|         leiomyosarcoma |
|         rhabdomyosarcoma |
|         colon carcinoma |
|         pancreatic cancer |
|         breast cancer |
|         ovarian cancer |
|         prostate cancer |
|         squamous cell carcinoma |
|         oral squamous cell carcinoma |
|         hepatocellular carcinoma |
|         basal cell carcinoma |
|         adenocarcinoma |
|         sweat gland carcinoma |
|         sebaceous gland carcinoma |
|         papillary carcinoma |
|         papillary adenocarcinomas |
|         cystadenocarcinoma |
|         medullary carcinoma |
|         bronchogenic carcinoma |
|         renal cell carcinoma |
|         hepatoma |
|         bile duct carcinoma |
|         choriocarcinoma |
|         seminoma |
|         embryonal carcinoma |
|         Wilms' tumor |
|         cervical cancer |
|         cervix adenocarcinoma |
|         uterine cancer |
|         testicular tumor |
|         lung carcinoma |
|         small cell lung carcinoma |
|         non-small cell lung adenocarcinoma |
|         bladder carcinoma |
|         epithelial carcinoma |
|         glioma |
|         malignant glioma |
|         glioblastoma multiforme |
|         astrocytic gliomas |
|         medulloblastoma |
|         craniopharyngioma |
|         ependymoma |
|         pinealoma |
|         hemangioblastoma |
|         acoustic neuroma |
|         oligodendroglioma |
|         meningioma |
|         melanoma |
|         neuroblastoma |
|         retinoblastoma |

In specific embodiments, cancer, malignancy or dysproliferative changes (such as metaplasias and dysplasias), or hyperproliferative disorders, are treatable or preventable in the ovary, breast, colon, lung, skin, pancreas, prostate, bladder, or uterus. In other specific embodiments, the cancer treatable or preventable by the administration of an effective amount of a Compound of the Invention is sarcoma, melanoma, or leukemia. In other specific embodiments, the cancer treatable or preventable by the administration of an effective amount of a Compound of the Invention is multiple myeloma, leukemia, a myelodysplastic syndrome or a myeloproliferative disorder. In another specific embodiment, the cancer treatable or preventable by the administration of an effective amount of a Compound of the Invention is a glioma.

In preferred embodiment, the Compounds of the Invention are useful for treating or preventing cancers including prostate (more preferably hormone-insensitive), Neuroblastoma, Lymphoma (preferably follicular or Diffuse Large B-cell), Breast (preferably Estrogen-receptor positive), Colorectal, Endometrial, Ovarian, Lymphoma (preferably non-Hodgkin's), Lung (preferably Small cell), or Testicular (preferably germ cell).

In another embodiment, the Compounds of the Invention are useful for inhibiting the growth of a cell derived from a cancer or neoplasm such as prostate (more preferably hormone-insensitive), Neuroblastoma, Lymphoma (preferably follicular or Diffuse Large B-cell), Breast (preferably Estrogen-receptor positive), Colorectal, Endometrial, Ovarian, Lymphoma (preferably non-Hodgkin's), Lung (preferably Small cell), or Testicular (preferably germ cell).

In specific embodiments of the invention, the Compound of the Invention are useful for inhibiting the growth of a cell, said cell being derived from a cancer or neoplasm in Table 2 or herein.

The compound of EXAMPLE 1 ((4-{[3-(2,2-Dimethyl-tetrahydro-pyran-4-yl)-4-phenyl-butylamino]-methyl}-phenyl)-dimethyl-amine), an illustrative example of the Compounds of the Invention, has been shown to induce cell (programmed) death in the following cell lines: Hela (cervix adenocarcinoma), MDA-MB-435 (breast cancer), MDA-MB-231 (breast cancer), MCF-7 (breast cancer), HL-60 (leukemia), A172 (malignant glioma), NCIH1703 (non-small cell lung adenocarcinoma), A357 (lung cancer), DU145 (prostate cancer), MM1s (multiple myeloma), DF15 (multiple myeloma), H929 (multiple myeloma), U266 (multiple myeloma), ANB6 (multiple myeloma).

4.10. Infectious Diseases Treatable or Preventable

Infectious diseases and related disorders that can be treated or prevented by administration of a Compound of the Invention include, but are not limited to, those listed in Table 3:

TABLE 3

INFECTIOUS DISEASES

Bacterial Diseases:

Diptheria
Pertussis
Occult Bacteremia
Urinary Tract Infection
Gastroenteritis
Cellulitis
Epiglottitis
Tracheitis
Adenoid Hypertrophy
Retropharyngeal Abcess
Impetigo
Ecthyma
Pneumonia
Endocarditis
Septic Arthritis
Pneumococcal
Peritonitis
Bactermia
Meningitis
Acute Purulent Meningitis
Urethritis
Cervicitis
Proctitis
Pharyngitis
Salpingitis
Epididymitis
Listeriosis
Anthrax
Nocardiosis
Salmonella
Typhoid Fever
Dysentery
Conjuntivitis
Sinusitis
Brucellosis
Tullaremia
Cholera
Bubonic Plague
Tetanus
Necrotizing Enteritis
Actinomycosis
Mixed Anaerobic Infections
Syphilis
Relapsing Fever
Leptospirosis
Lyme Disease
Rat Bite Fever
Tuberculosis
Lymphadenitis
Leprosy
Systemic Fungal Diseases:

Histoplamosis
Coccicidiodomycosis
Blastomycosis
Sporotrichosis
Cryptococcsis
Systemic Candidiasis TABLE 3-continued

INFECTIOUS DISEASES

Aspergillosis
Mucormycosis
Mycetoma
Chromomycosis
Rickettsial Diseases:

Typhus
Rocky Mountain Spotted Fever
Ehrlichiosis
Eastern Tick-Borne Rickettsioses
Rickettsialpox
Q Fever
Bartonellosis
Chlamydial Diseases Chlamydia
Chlamydial Pnenmonia
Trachoma
Inclusion Conjunctivitis
Parasitic Diseases:

Malaria
Babesiosis
African Sleeping Sickness
Chagas' Disease
Leishmaniasis
Dum-Dum Fever
Toxoplasmosis
Meningoencephalitis
Keratitis
Entamebiasis
Giardiasis
Cryptosporidiasis
Isosporiasis
Cyclosporiasis
Microsporidiosis
Ascariasis
Whipworm Infection
Hookworm Infection
Threadworm Infection
Ocular Larva Migrans
Trichinosis
Guinea Worm Disease
Lymphatic Filariasis
Loiasis
River Blindness
Canine Heartworm Infection
Schistosomiasis
Swimmer's Itch
Oriental Lung Fluke
Oriental Liver Fluke
Fascioliasis
Fasciolopsiasis
Opisthorchiasis
Tapeworm Infections
Hydatid Disease
Alveolar Hydatid Disease
Viral Diseases:

Measles
Subacute sclerosing panencephalitis
Common Cold
Mumps
Rubella
Roseola
Fifth Disease
Chickenpox
Respiratory syncytial virus infection
Croup
Bronchiolitis
Infectious Mononucleosis
Poliomyelitis
Herpangina
Hand-Foot-and-Mouth Disease
Bornholm Disease
Aseptic Meningitis
Myocarditis

TABLE 3-continued

INFECTIOUS DISEASES

Pericarditis
Gastroenteritis
Acquired Immunodeficiency Syndrome (AIDS)
Reye's Syndrome
Fever of Unknown Origin
Kawasaki Syndrome
Pinworm Infestation
Influenza
Bronchitis
Viral "Walking" Pneumonia
Acute Febrile Respiratory Disease
Acute pharyngoconjunctival fever
Epidemic keratoconjunctivitis
Herpes Simplex Virus 1 (HSV-1)
Herpes Simples Virus 2 (HSV-2)
Shingles
Cytomegalic Inclusion Disease
Rabies
Progressive Multifocal Leukoencephalopathy
Prion Diseases
Kuru
Fatal Familial Insomnia
Creutzfeldt-Jakob Disease
Gerstmann-Straussler-Scheinker Disease
Tropical Spastic Paraparesis
Western Equine Encephalitis
California Encephalitis
St. Louis Encephalitis
Yellow Fever
Dengue
Lymphocytic choriomeningitis
Lassa Fever
Hemorrhagic Fever
Hantvirus Pulmonary Syndrome
Marburg Virus Infections
Ebola Virus Infections
Smallpox
Sexually Transmitted Diseases:

Gonorrhea
Syphilis
Genital Candidiasis
Chancoid
Balanoposthitis
Genital Herpes
Genital Warts
Sexually Transmitted Enteric Infections Therapeutic agents useful in the treatment of infectious diseases that may be used in combination with a Compound of the Invention include, but are not limited to, a penicillin, a cephalosporin, vancomycin, an aminoglycoside, a quinolone, a polymyxin, erythromycin, a tetracycline, chloramphenicol, clindamycin, lincomycin, clarithromycin, azithromycin, a sulfonamide, idoxuridine, vidarabine, trifluorothymidine, acyclovir, penciclovir, and valacyclovir.

4.11. Inflammatory Diseases Treatable or Preventable

Inflammatory diseases and related disorders that can be treated or prevented by administration of a Compound of the Invention include, but are not limited to, rheumatoid arthritis, connective tissue disease, inflammatory bowel disease, Crohn's Disease, ulcerative colitis and ileitis.

Therapeutic agents useful in the treatment of inflammatory diseases that may be used in combination with a Compound of the Invention include, but are not limited to, an anticholinergic, diphenoxylate, loperamide, deodorized, opium tincture, codeine and hydrophilic mucilloids.

4.12. Cardiovascular Diseases Treatable or Preventable

Cardiovascular diseases and related disorders that can be treated or prevented by administration of a Compound of the Invention include, but are not limited to, hypercholesterolemia, arterial hypertension, arteriosclerosis, coronary artery disease, arrhythmia, valvular heart disease, endocarditis and pericardial disease.

Therapeutic agents useful in the treatment of cardiovascular diseases that may be used in combination with a Compound of the Invention include, but are not limited to, antibiotics, folic acid and antihypertensive drugs.

4.13. Immune Disorders Treatable or Preventable

Immune disorders that can be treated or prevented by administration of a Compound of the Invention include, but are not limited to, allergy, asthma, chronic granulomatous, autoimmune disorders, Wegener's granulomatosis, systemic lupus erythematosus, multiple sclerosis, type 1 diabetes mellitus, rheumatoid arthritis, graft versus host disease, rheumatic heart disease and DiGeorge anomaly.

Therapeutic agents useful in the treatment of immune disorders that may be used in combination with a Compound of the Invention include, but are not limited to, gamma interferon, glucocorticoid and cyclophosphamide.

4.14. Compounds of the Invention Useful as Preservatives for a Cell, Blood, Tissue, an Organ or an Organism The use of Compounds of the Invention as an inhibitor of cell growth makes them useful as agents useful to preserve blood, tissue or an organ is in a condition suitable for use in a patient. In particular, the Compounds of the Invention are useful to extend the lifetime of a cell, blood, tissue, an organ or an organism that is cryopreserved, e.g., frozen in liquid nitrogen, frozen with in dry ice, frozen in ice water or a frozen with a cold-pack.

5. EXAMPLES

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

The following conditions were used to obtain HPLC retention times in connection with synthetic examples 1–24:

| | |
|---|---|
| Column: | YMC Pack-Pro C18 250 mm × 4.6 mm ID<br>Run 20 minutes total, 0–10 mins gradient indicated, 10–20 mins isocratic Detection at 214 nm, 254 nm and 290 nm. |
| Gradients: | 25–75% acetonitrile-water/0.1% TFA<br>25–95% acetonitrile-water/0.1% TFA |

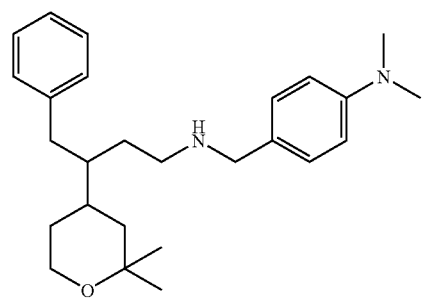

Example 1

5.1 EXAMPLE 1

(4-({[3-(2',2'-dimethyltetrahydropyran-4'-yl)-4-phenylbutylamino]-methyl}-phenyl)-dimethylamine dihydrochloride

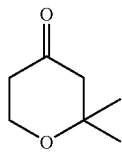

1(A)

1(A). 2,2-dimethyl-tetrahydropyran-4-one

Mesityl oxide (11.6 mmol) and aqueous formaldehyde (11.6 mmol) were combined and heated at 165° C. for 2 hours. The reaction mixture was cooled, partitioned between ethyl acetate and brine, dried over sodium sulfate and evaporated to an oil. The crude reaction product was subjected to flash column chromatography (silica gel) eluting with ethyl acetate-hexane (1:9) to give an oil. The oil was dissolved in chloroform (250 ml), amberlyst 15 resin (11 g) was added and the mixture stirred for about 16 hours. Filtration and evaporation yielded the crude product which was subjected to flash column chromatography (silica gel) eluting with diethyl ether-hexane (1:9) to give the desired product.

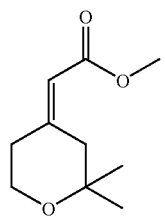

1(B)

1(B). (E) and (Z) methyl (2,2-dimethyl-tetrahydropyran-4-ylidene)acetate

To sodium hydride (23.8 mmol) in THF (80 ml) at 0° C. was added trimethyl phosphonoacetate (22.86 mmol). The reaction mixture was stirred for 15 minutes and a solution of example1(A) (20.6 mmol) in THF (20 ml) was added. After 20 hours at ambient temperature the reaction was quenched by addition of an aqueous ammonium chloride solution. Extraction with ethyl acetate, drying (sodium sulfate) and evaporation yielded the crude product. Purification by flash column chromatography (silica gel) eluting with ethyl acetate-hexane (1:5) gave the desired product.

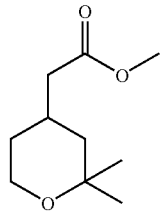

1(C)

1(C). Methyl (2',2'-dimethyltetrahydropyran-4'-yl)acetate

To Example1(B) (17.9 mmol) in ethyl acetate (35 ml) was added 10% palladium-on-carbon (10 mol %) and then subjected to hydrogenation. After 3 hours at ambient temperature the catalyst was filtered off, the reaction mixture then evaporated in vacuo to give the desired material.

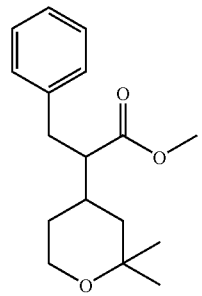

1(D)

1(D). Methyl 2-(2',2'-dimethyltetrahydropyran-4'-yl)-3-phenylpropionate

To di-isopropylamine (22.5 mmol) in THF (10 ml) at −78° C. was added butyllithium (22.4 mmol), the reaction warmed to 0° C. for 5 minutes before re-cooling to −78° C. A solution of example 1(C) (16.1 mmol) in THF (25 ml) was then added slowly to the preformed LDA solution. After 1 hour at −78° C. benzyl bromide (17.6 mmol) was added and the reaction mixture warmed to ambient temperature over a period of 30 minutes. Addition of aqueous ammonium chloride solution, extraction with ethyl acetate, brine wash and drying (sodium sulfate) followed by evaporation yielded the crude product. Purification by flash column column chromatography (silica gel) eluting with ethyl acetate-hexane (1:3) gave the desired product.

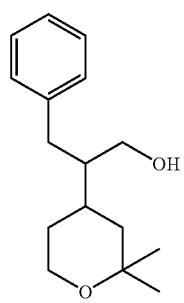

1(E)

1(E). 2-(2',2'-dimethyltetrahydropyran-4'-yl)-3-phenylpropan-1-ol

To a solution of example 1(D) (10.9 mmol) in dichloromethane (35 ml) at −78° C. was added 1.0M DIBAL (27.0 mmol). The reaction was immediately allowed to warm to ambient temperature whereupon the reaction was quenched with 1N HCl. Extraction with ethyl acetate, brine wash and drying (sodium sulfate) followed by evaporation yielded the crude product. Purification by flash column chromatography (silica gel) eluting with diethyl ether-hexane (1:1) gave the desired product.

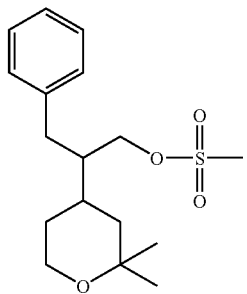

1(F)

1(F). 2-(2',2'-dimethyltetrahydropyran-4'-yl)-3-phenylpropan-1-ol methanesulfonate To a solution of example 1 (E) (10.4 mmol) in dichloromethane (40 ml) was added di-isopropylethylamine (15.5 mmol) followed by methanesulfonyl chloride (11.6 mmol). After 2 hours the reaction was partitioned between water and ethyl acetate, washed with 1N HCl, brine and dried (sodium sulfate) and evaporated in vacuo to yield the crude product. Purification by flash column chromatography (silica gel) eluting with diethyl ether-hexane (1:1) gave the desired product.

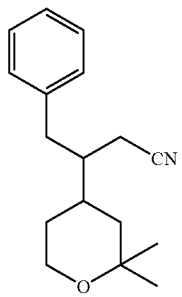

1(G)

1(G). 3-(2',2'-dimethyltetrahydropyran-4'-yl)-4-phenylbutyronitrile

To a solution of example 1(F) (9.90 mmol) in DMF (20 ml) was added sodium cyanide (10.6 mmol). The reaction was stirred at 100° C. for 6 hours before partitioning it between water and ethyl acetate, washing with brine, drying (sodium sulfate) and evaporation yielded the crude product. Purification by flash column chromatography (silica gel) eluting with diethyl ether-hexane (1:1) gave the desired product.

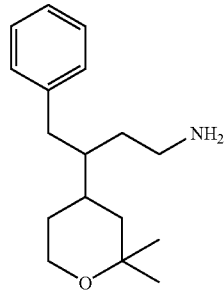

1(H)

1(H). 3-(2',2'-dimethyltetrahydropyran-4'-yl)-4-phenylbutylamine

To a solution of example 1(G) (8.37 mmol) in THF (40 ml) at 0° C. was added lithium aluminum hydride (11.85 mmol). The reaction was stirred for 16 hours, warming to ambient temperature before being quenched by sequential additions of water (0.45 ml), 3N NaOH (0.45 ml), water (1.3 ml). The reaction was filtered through Celite® and evaporated to an oil. Purification by flash column chromatography (silica gel) eluting with ethyl acetate: methanol: ammonium hydroxide (90:10:1) gave the desired product.

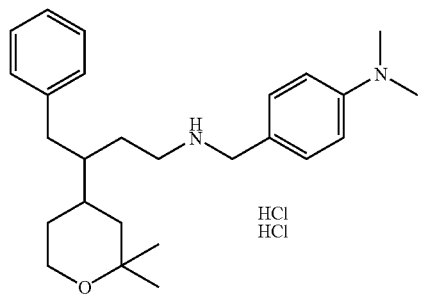

1(I)

1(I). (4-{[3-(2',2'-dimethyltetrahydropyran-4'-yl)-4-phenylbutylamino]-methyl}-phenyl)-dimethylamine dihydrochloride To a solution of example 1(H) (1.09 mmol) in dichloromethane (5 ml) was added magnesium sulfate and 4-dimethylamino-benzaldehyde (1.09 mmol), and the reaction was stirred at ambient temperature for 16 hours. The reaction mixture was filtered to remove magnesium sulfate and evaporated to yield the crude imine product. This was immediately dissolved in methanol (5 ml) and sodium borohydride (4.20 mmol) was added. The reaction was quenched by addition of water, evaporated to a small volume and extracted with ethyl acetate. Following a brine wash and drying (sodium sulfate), evaporation yielded the crude product. Purification by flash column chromatography (silica gel) eluting with ethyl acetate: methanol: ammonium hydroxide (90:10:1) gave the desired free base. Dissolution in diethyl ether, addition of a solution of HCl (gas) in diethyl ether generated a precipitate. This was filtered off, triturated with acetone and subsequent re-crystallization of the solid from boiling propan-2-ol yielded the desired di-hydrochloride salt as a white solid: m.p. 191–193° C.; C 66.80 H 8.62 N 5.99 Cl 15.17% calculated for $C_{26}H_{38}N_2O.2HCl$ found C66.94 H 8.45 N 5.92 Cl 14.95%; HPLC: 9.00 mins (25–75%); MS (e/z): 395 (M+1).

Following the outlined procedures for EXAMPLE 1, using any of the intermediates 1(A) to 1(H) inclusive, commercially available substituted acetic acids, substituted acetic esters, or cyclic ketones, the following examples, which are illustrative examples of the Compounds of the Invention, may be prepared using the protocols outlined above by one skilled in the art.

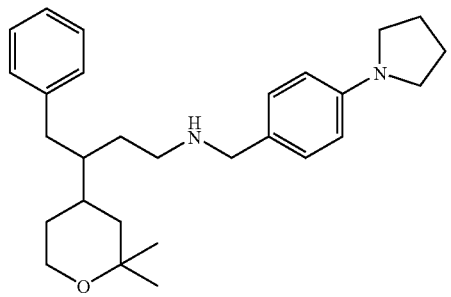

Example 2

5.2 EXAMPLE 2

(4-{[3-(2,2-dimethyltetrahydropyran-4-y1)-4-phenyl-butyl]-(4-pyrrolidin-1-y1-benzyl)-amine: HPLC: 12.45 mins (25–75%); MS (e/z):421 (M+1).

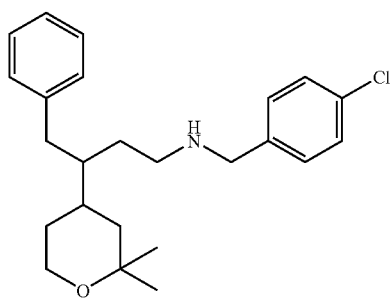

Example 3

5.3 EXAMPLE 3

(4-chloro-benzyl)-[3-(2,2-dimethyltetrahydropyran-4-y1)-4-phenyl-butyl]-amine: HPLC: 10.37 mins (25–95%); MS (e/z): 385 (M+1).

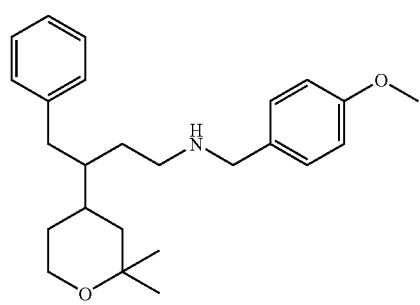

Example 4

5.4 EXAMPLE 4

[3-(2,2-dimethyltetrahydropyran-4-phenyl-butyl]-4-methoxy-benzyl)amine: HPLC: 9.49 mins (25–95%); MS (e/z): 382 (M+1).

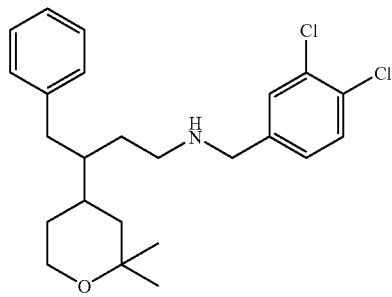

Example 5

5.5 EXAMPLE 5

(3,4-dichloro-benzyl-[3-(2,2-dimethylterahydropyran-4y1)-4-phenyl-butyl]-amine: HPLC: 11.21 mins (25–95%); MS (e/z): 420 (M+1).

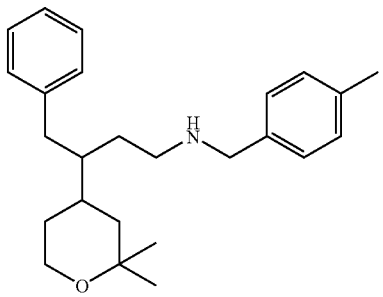

Example 6

5.6 EXAMPLE 6

[3-(2,2-dimethyltetrahydropyran-4-y1)-4-phenyl-butyl]-(4-methyl-benzyl)amine: HPLC: 11.79 mins (25–75%); MS (e/z): 366 (M+1).

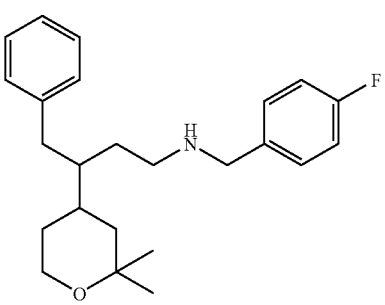

Example 7

5.7 EXAMPLE 7

[3-(2,2-dimethyltetrahydropyran-4-y1)-4-phenyl-butyl]-(4-fluro-benzyl)amine: HPLC: 11.34 mins (25–75%); MS (e/z): 370 (M+1).

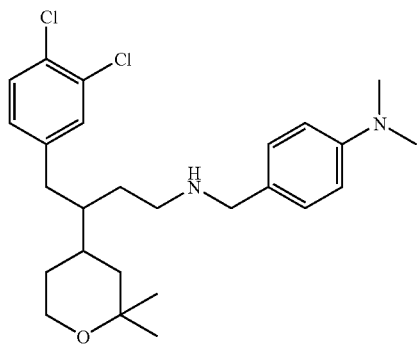

Example 8

5.8 EXAMPLE 8

(4-{[4-(3,4-dichloro-phenyl)-3-(2,2-dimethyltetrahydropyran-4-y1)-4-phenyl-butylamino]-methyl}-phenyl)-dimethyl-amine: HPLC: 10.75 mins (25–75%); MS (e/z): 463 (M+1).

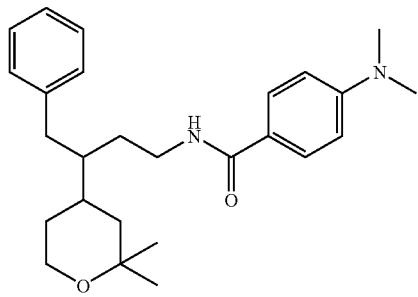

Example 9

5.9 EXAMPLE 9

4dimethylamino-N-[3-(2,2-dimethyltetrahydropyran-4-y1)-4-phenyl-butyl]-benzamide: HPLC: 14.27 mins (25–75%); MS (e/z): 409 (M+1).

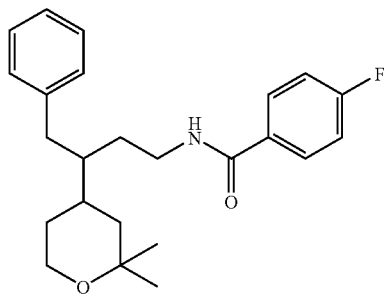

Example 10

5.10 EXAMPLE 10

N-[3-(2,2-dimethyltetrahydropyran-4-phenyl-butyl]-4-fluro-benzamide: HPLC: 16.80 mins (25–75%); MS (e/z): 384 (M+1).

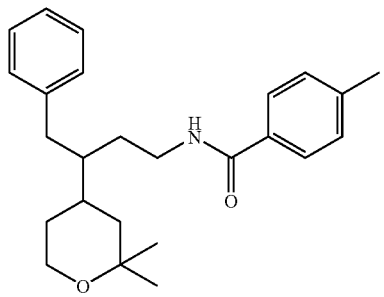

Example 11

5.11 EXAMPLE 11

N-[3-(2,2-dimethyltetrahydropyran-4-y1)-4-phenyl-butyl]-4-methyl-benzaamide: HPLC: 17.42 mins (25–75%); MS (e/z): 380 (M+1).

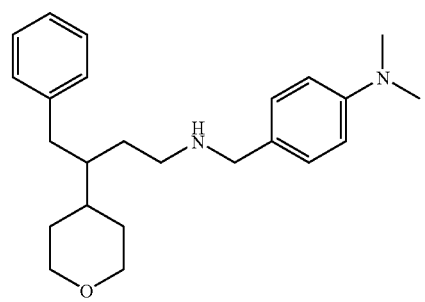

Example 12

5.12 EXAMPLE 12 dimethyl-(4-{[4-phenyl-3-(2,2-dimethyltetrahydropyran-4-y1)-butylamino]-methyl}-phenyl)-amine: HPLC: 8.13 mins (25–75%); MS (e/z): 367 (M+1).

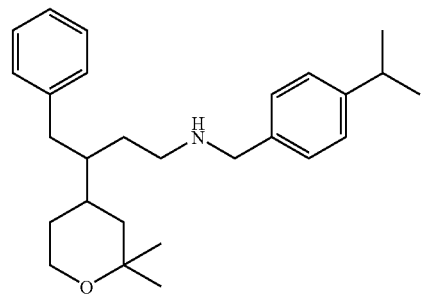

Example 13

5.13 EXAMPLE 13

[3-(2,2-dimethyltetrahydropyran-4-yl)-4-phenyl-butyl]-(4-isopropyl-benzyl-amine: HPLC: 14.32 mins (25–75%); MS (e/z): 394 (M+1).

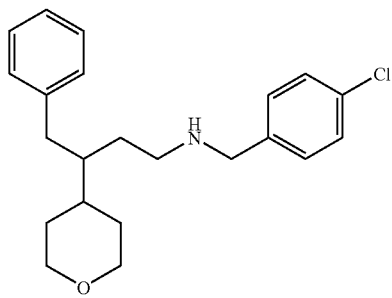

Example 14

5.14 EXAMPLE 14

(4-chloro-benzyl)-[4-phenyl-3-(2,2-dimethyltetrahydropyran-4-yl)-butyl]-amine: HPLC: 11.14 mins (25–75%); MS (e/z): 358 (M+1).

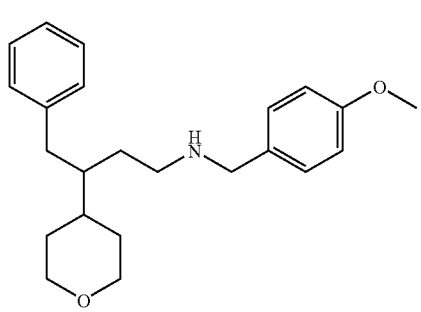

Example 15

5.15 EXAMPLE 15

(4-methoxy-benzyl)-[4-phenyl-3-(2,2-dimethyltetrahydropyran-4-yl)-butyl]-amine: HPLC: 10.54 mins (25–75%); MS (e/z): 354 (M+1).

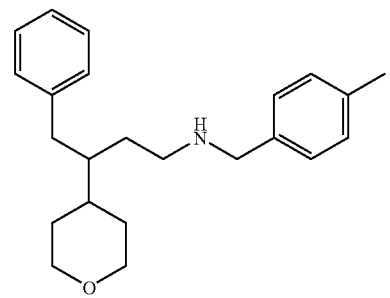

Example 16

5.16 EXAMPLE 16

(4-methyl-benzyl)-[4-phenyl-3-(2,2m-dimethyltetrahydropyran-4-yl]-amine: HPLC: 11.03 mins (25–75%); MS (e/z): 338 (M+1).

Example 17

5.17 EXAMPLE 17 benzyl-[4-phenyl-3-(2,2-dimethyltetrahydropyran-4-yl)-butyl]-amine: HPLC: 10.45 mins (25–75%); MS (e/z): 324 (M+1).

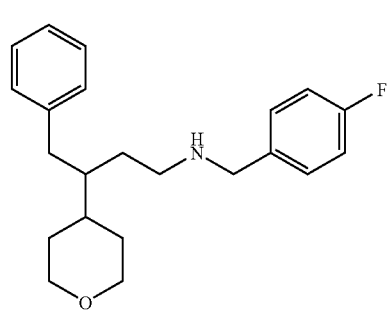

Example 18

5.18 EXAMPLE 18

(4-fluro-benzyl)-[4-phenyl-3-(2,2-dimethyltetrahydropyran-4-yl)-butyl]-amine: HPLC: 10.84 mins (25–75%); MS (e/z): 342 (M+1).

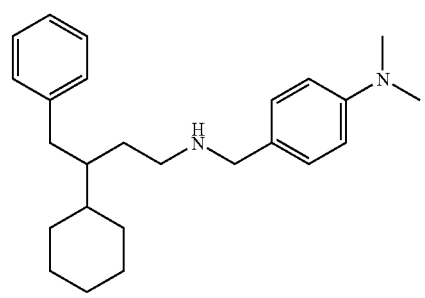

Example 19

5.19 EXAMPLE 19

{4-[(3-cyclohexyl-4-phenyl-butylamino)-methyl]-phenyl}-dimethyl-amine: HPLC: 11.60 mins (25–75%); MS (e/z): 365 (M+1).

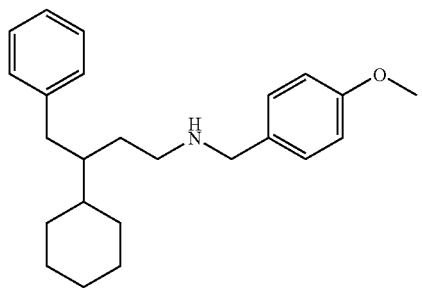

Example 20

5.20 EXAMPLE 20

(3-cyclohexyl-4-phenyl-butyl)-(4-methoxy-benzyl)-amine: HPLC: 13.63 mins (25–75%); MS (c/z): 352 (M+1).

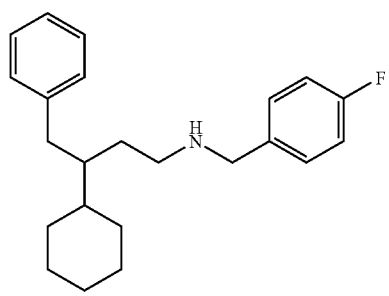

Example 21

5.21 EXAMPLE 21

(3-cyclohexyl-4-phenyl-butyl)-(4-fluoro-benzyl)-amine: HPLC: 13.65 mins (25–75%); MS (e/z): 340 (M+1).

Example 22

5.22 EXAMPLE 22

(4-{[3-cyclohexyl-4-(3,4-dichlorophenyl)-butylamino]-methyl}-phenyl)-dimethyl-amine: HPLC: 12.94 mins (25–75%); MS (e/z): 435 (M+1).

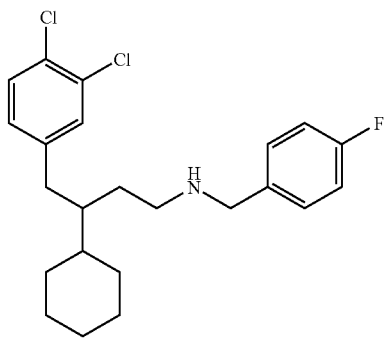

Example 23

5.23 EXAMPLE 23

[3-cyclohexyl-4-(3,4-dichlorophenyl)-butyl]-(4-fluoro-benzyl)-amine: HPLC: 14.73 mins (25–75%); MS (e/z): 408 (M+1).

Example 24

5.24 EXAMPLE 24 dimethyl-(4-{[3-phenyl-3-(2,2-dimethyltetrahydro-pyran-4-yl)-propylamino]-methyl}phenyl)-amine: HPLC: 7.90 mins (25–75%); MS (e/z): 353 (M+1).

5.25 EXAMPLE 25

In Vitro Assay Demonstrating that the Compound of Example 1 Induces G1 Arrest in MDA-435 Cells Methods An in vitro cell cycle assay was used to demonstrate that a Compound of the Invention induces cell-cycle arrest in MDA-435 human breast cancer cells. Tumor cells were synchronized by serum deprivation for 24 hours, then released by adding 10% serum to the cell culture with either the compound of EXAMPLE 1 ((4-{[3-(2,2-Dimethyl-tetrahydro-pyran-4-yl)-4-phenyl-butylamino]-methyl}-phenyl)-dimethyl-amine) (obtained from ChemBridge Corporation; single peak via HPLC: 20–100% gradient:

acetonitrile/water/1% trifluoroacetic acid) or vehicle (dimethylsofloxide). Cells were harvested and stained in 0.04% digitonin working solution with 50 mg/ml propidium iodide. DNA content was analyzed by Flow Cytometry (Coulter). The population of cells in each phase was determined using Expo 32-ADC Software for Coulter EPICS® XL™ Cytometers, version 1.1 B (2001).

Results

MDA-435 human breast cancer cells that were treated with the compound of EXAMPLE 1 had $G_0/G_1$ to S phase transition blocked more efficiently than vehicle (38% phase transition blockage for cells treated with the compound of EXAMPLE 1 compared to 28% phase transition blockage for cells treated with vehicle). Thus, the compound of EXAMPLE 1, an illustrative example of the Compounds of the Invention, significantly arrests the cell cycle and, accordingly, is useful for treating or preventing human breast cancer.

5.26 EXAMPLE 26

In Vitro Assay Demonstrating that the Compound of Example 1 Induces Apoptosis in MDA-435 Tumor Cells Methods MDA-435 human breast cancer cells were treated with either vehicle or varying doses of the compound of EXAMPLE 1. Cells were harvested and stained with Annexin V-FITC and PI by Flow Cytometry using ApoAlert Annexin V-FITC apoptosis kit (Clonetech, BD). The percentage of apoptotic cells were determined using EPICS® XL™ and XL-MCL, System II™ Software, version 1.0 (1996).

Results

The compound of EXAMPLE 1 dose-dependently increases the intensity of Annexin V-FITC staining of up to 30% of the cell population. Annexin V is a 36 kD $Ca^{2+}$ protein that has a strong affinity for phosphatidylserin (PS). In non-apoptic cells, most PS molecules are localized in the inner layer of the plasma membrane. During apoptosis, PS redistributes to the outer layer of the membrane. Externalization of PS can be detected by fluorochrome conjugated Annexin V. This demonstrates that the compound of EXAMPLE 1, an illustrative example of the Compounds of the Invention, induces apoptosis and, accordingly, is useful for treating or preventing cancer, particularly human breast cancer.

PI is a fluorescent dye that stains DNA. PI does not cross the plasma membrane in viable cells. In contrast, cells in a late stage of apoptosis lose their integrity and therefore are permeable to PI. The increase in PI staining of cells treated with the compound of EXAMPLE 1 is further evidence of its ability to induce apoptosis and usefulness for treating or preventing cancer.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited, the entire disclosures of which are incorporated herein by reference in their entirety.

What is claimed is:

1. A method for treating breast, ovary, testicle, prostate, head, neck, eye, skin, mouth, throat, esophagus, chest, bone, lung, colon, sigmoid, rectum, stomach, kidney, liver, pancreas, brain, intestine, heart or adrenal cancer or neoplastic disease comprising administering to a patient in need of such treatment an effective amount of a compound of formula (I):

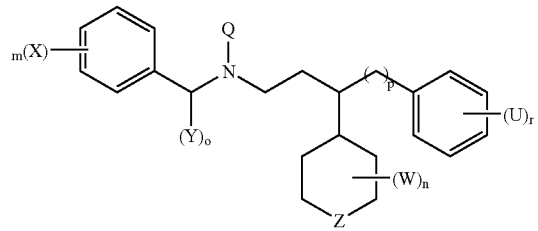

wherein:

X, W and U are at each occurrence independently H, halogen, hydroxy, carboxy, alkoxy, alkylamino, branched or unbranched $C_{1-10}$ alkyl, $C_2$–$C_{10}$ alkenyl, $C_2$–$C_{10}$ alkynyl, haloalkyl, acyloxy, thioalkyl, sulfonyl, sulfinylalkyl, sulfonylalkyl, hydroxyalkyl, substituted or unsubstituted aryl, substituted or unsubstituted heteroaryl, substituted or unsubstituted heterocycle, substituted or unsubstituted cycloalkyl, —C(=O)OR$_1$, —OC(=O)R$_1$, —C(=O)NR$_1$R$_2$, —C(=O)NR$_1$OR$_2$, —SO$_2$NR$_1$R$_2$, —NR$_1$SO$_2$R$_2$, —CN, —NO$_2$, —NR$_1$R$_2$, —NR$_1$C(=O)R$_2$, —NR$_1$C(=O)(CH$_2$)$_q$OR$_2$, —NR$_1$C(=O)(CH$_2$)$_q$R$_2$, NR$_1$C(=O)(CH$_2$)$_q$NR$_1$R$_2$, —O(CH$_2$)$_q$NR$_1$R$_2$;

$R_1$ and $R_2$ are independently H or branched or unbranched $C_1$–$C_{10}$ alkyl;

Y at each occurrence is independently H, branched or unbranched $C_1$–$C_{10}$ alkyl, or when o is 1, Y can be (=O);

Z is C or O;

Q is H, branched or unbranched $C_1$–$C_{10}$ alkyl;

m is 0–5;

n is 0–8;

o is 0–2;

p is 0–2;

q is 0–5; and r is 0–5;

or a pharmaceutically acceptable salt thereof.

2. A method for inhibiting the growth of a breast, ovary, testicle, prostate, head, neck, eye, skin, mouth, throat, esophagus, chest, bone, lung, colon, sigmoid, rectum, stomach, kidney, liver, pancreas, brain, intestine, heart or adrenal cancer or neoplastic cell comprising contacting said cancer cell or neoplastic cell with an effective amount of a compound of formula (I):

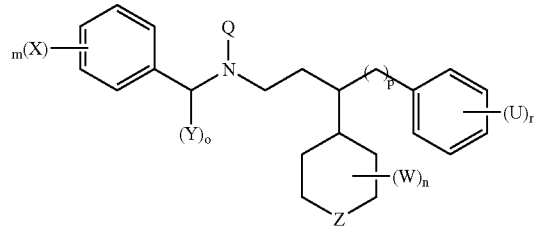

wherein:

X, W and U are at each occurrence independently H, halogen, hydroxy, carboxy, alkoxy, alkylamino, branched or unbranched $C_1$–$C_{10}$ alkyl, $C_2$–$C_{10}$ alkenyl, $C_2$–$C_{10}$ alkynyl, haloalkyl, acyloxy, thioalkyl, sulfonyl, sulfinylalkyl, sulfonylalkyl, hydroxyalkyl, substituted or unsubstituted aryl, substituted or unsubstituted heteroaryl, substituted or unsubstituted heterocycle, substituted or unsubstituted cycloalkyl, —C(=O)OR$_1$, —OC(=O)R$_1$, —C(=O)NR$_1$R$_2$, —C(=O)NR$_1$OR$_2$, —SO$_2$NR$_1$R$_2$, —NR$_1$SO$_2$R$_2$, —CN, —NO$_2$, —NR$_1$R$_2$, —NR$_1$C(=O)R$_2$, —NR$_1$C(=O)(CH$_2$)$_q$OR$_2$, —NR$_1$C(=O)(CH$_2$)$_q$R$_2$, NR$_1$C(=O)(CH$_2$)$_q$NR$_1$R$_2$, —O(CH$_2$)$_q$NR$_1$R$_2$;

R$_1$ and R$_2$ are independently H or branched or unbranched $C_1$–$C_{10}$ alkyl;

Y at each occurrence is independently H, branched or unbranched $C_1$–$C_{10}$ alkyl, or when o is 1, Y can be (=O);

Z is C or O;

Q is H, branched or unbranched $C_1$–$C_{10}$ alkyl;

m is 0–5;

n is 0–8;

o is 0–2;

p is 0–2;

q is 0–5; and r is 0–5;

or a pharmaceutically acceptable salt thereof.

* * * * *